US012745967B2

(12) United States Patent
Maidment et al.

(10) Patent No.: US 12,745,967 B2
(45) Date of Patent: Sep. 29, 2026

(54) DYNAMIC FOUR-DIMENSIONAL CONTRAST ENHANCED TOMOSYNTHESIS

(71) Applicants: The Trustees of the University of Pennsylvania, Philadelphia, PA (US); Real Time Tomography, LLC, Villanova, PA (US)

(72) Inventors: Andrew D. A. Maidment, Villanova, PA (US); Brian Lee, Rockville, MD (US); Susan Ng, Villanova, PA (US); Peter A. Ringer, Allentown, PA (US); Johnny Kuo, Lancaster, PA (US); Raymond J. Acciavatti, Newtown Square, PA (US)

(73) Assignees: The Trustees of the University of Pennsylvania, Philadelphia, PA (US); Real Time Tomography, LLC, Villanova, PA (US)

( * ) Notice: Subject to any disclaimer, the term of this patent is extended or adjusted under 35 U.S.C. 154(b) by 73 days.

(21) Appl. No.: 18/061,928

(22) Filed: Dec. 5, 2022

(65) Prior Publication Data

US 2023/0240625 A1 Aug. 3, 2023

Related U.S. Application Data

(63) Continuation of application No. 15/101,668, filed as application No. PCT/US2014/068610 on Dec. 4, 2014, now Pat. No. 11,517,270.

(Continued)

(51) Int. Cl.

| | |
|---|---|
| ***A61B 6/02*** | (2006.01) |
| ***A61B 6/00*** | (2024.01) |

(Continued)

(52) U.S. Cl.

CPC ............ *A61B 6/025* (2013.01); *A61B 6/4452* (2013.01); *A61B 6/461* (2013.01); *A61B 6/481* (2013.01);

(Continued)

(58) Field of Classification Search

CPC ....... A61B 6/025; A61B 6/4452; A61B 6/461; A61B 6/481; A61B 6/502; A61B 6/505; A61B 6/5235; A61B 6/54; G06T 7/0012

See application file for complete search history.

(56) References Cited

U.S. PATENT DOCUMENTS

| | | |
|---|---|---|
| 8,155,729 B1 | 4/2012 | Hsieh et al. |
| 8,233,690 B2 | 7/2012 | Ng et al. |

(Continued)

FOREIGN PATENT DOCUMENTS

| | | |
|---|---|---|
| DE | 102012203751 A1 | 9/2013 |
| WO | 2014/011681 A2 | 1/2014 |
| WO | 2015/126504 A2 | 8/2015 |

OTHER PUBLICATIONS

Acciavatti et al., "Observation of super-resolution in digital breast tomosynthesis", Medical Physics, 2012, vol. 39, No. 12, pp. 7518-7539.

(Continued)

*Primary Examiner* — Kaitlyn E Sebastian

(74) *Attorney, Agent, or Firm* — BakerHostetler

(57) ABSTRACT

A contrast-enhanced digital tomosynthesis system with a source configured to emit penetrating particles toward an source, a positioning apparatus configured to position the source relative to the object and the detector, and an imaging system coupled to the source, the detector, and the positioning apparatus. The imaging system is configured to control the positioning apparatus to position the source and detector relative to the object, control the source and the detector to (Continued)

acquire the series of projection images, and construct a tomographic volume capable of exhibiting super-resolution morphology and contrast-enhancement arising from injection of an exogenous contrast agent from data representing the acquired series of projection images or a subset thereof.

24 Claims, 22 Drawing Sheets

Related U.S. Application Data

(60) Provisional application No. 61/911,761, filed on Dec. 4, 2013.

(51) Int. Cl.
*A61B 6/46* (2024.01)
*A61B 6/50* (2024.01)
*G06T 7/00* (2017.01)

(52) U.S. Cl.
CPC .............. *A61B 6/502* (2013.01); *A61B 6/505* (2013.01); *A61B 6/5235* (2013.01); *A61B 6/54* (2013.01); *G06T 7/0012* (2013.01)

(56) References Cited

U.S. PATENT DOCUMENTS

2002/0196893 A1 12/2002 Gordon
2003/0215120 A1 11/2003 Uppaluri et al.
2004/0174960 A1 9/2004 Hsieh et al.
2005/0008124 A1* 1/2005 Ullberg .................. A61B 6/025 378/197
2005/0063611 A1* 3/2005 Toki ..................... G01N 23/046 382/299
2005/0075563 A1* 4/2005 Sukovic ................. A61B 6/469 600/427
2005/0113681 A1 5/2005 Defreitas et al.
2006/0098855 A1 5/2006 Gkanatsios et al.
2006/0108509 A1 5/2006 Frangioni et al.
2006/0269114 A1* 11/2006 Metz ..................... G06T 11/008 382/131
2007/0098141 A1* 5/2007 Hjarn ....................... A61B 6/02 378/37
2008/0015448 A1 1/2008 Keely et al.
2008/0181355 A1 7/2008 Hemmendorff et al.
2008/0187094 A1 8/2008 Stodilka et al.
2008/0240533 A1* 10/2008 Piron ........................ G06T 5/50 382/131
2009/0041179 A1 2/2009 Zellerhoff
2009/0080765 A1* 3/2009 Bernard ................ G06T 11/008 382/128
2009/0175562 A1 7/2009 Pan et al.
2011/0150308 A1 6/2011 Thibault et al.
2012/0022401 A1* 1/2012 Fischer .............. A61B 10/0233 600/567
2013/0237815 A1 9/2013 Klingenbeck
2013/0253895 A1 9/2013 Okell et al.
2013/0296737 A1 11/2013 Mcmillan et al.
2013/0336450 A1* 12/2013 Kyriakou ................ A61B 5/33 378/62
2015/0069257 A1 3/2015 Besson
2016/0302742 A1 10/2016 Maidment et al.
2019/0259187 A1 8/2019 Heese et al.
2021/0177371 A1 6/2021 Wang et al.

OTHER PUBLICATIONS

Carton et al., "Optimization of a dual-energy contrast-enhanced technique for a photon counting digital-breast tomosynthesis system", Medical Physics, 2010, vol. 37, No. 11, pp. 5896-5907.
International Preliminary Report on Patentability for PCT/US2014/068610 mailed Jun. 16, 2016.
International Search Report for PCT/US14/68610 mailed Sep. 30, 2015.

* cited by examiner

1000

DYNAMIC FOUR-DIMENSIONAL CONTRAST ENHANCED TOMOSYNTHESIS

CROSS-REFERENCE TO RELATED APPLICATIONS

This application is a continuation of U.S. application Ser. No. 15/101,668 filed Jun. 3, 2016, which is the U.S. national phase application of International Patent Application No. PCT/US2014/068610 filed Dec. 4, 2014, which claims priority to U.S. Provisional Application No. 61/911,761 filed Dec. 4, 2013, each of which are incorporated by reference in their entirety for any and all purposes.

STATEMENT REGARDING FEDERALLY SPONSORED RESEARCH

This invention was made with government support under W81XWH-11-1-0229 awarded by the Medical Research and Development Command. The government has certain rights in the invention.

BACKGROUND OF THE INVENTION

The need for a medical imaging modality that overcomes the obscuration of overlapping bodily features has given rise to digital tomosynthesis, a three-dimensional (3D) x-ray imaging technique used for cancer screening and diagnosis. However, 3D tomosynthesis is limited in the detection of structures that do not demonstrate readily discernible radiographic features, such as tumor bloodflow. Modalities like magnetic resonance imaging (MRI) are sensitive to the abnormal metabolic activity of tumor tissue but do not have the anatomical resolution of tomosynthesis.

SUMMARY OF THE INVENTION

Aspects of the invention include a contrast-enhanced digital tomosynthesis system. The system may include a source configured to emit penetrating particles toward an object, a detector configured to acquire a series of projection images of the object in response to the penetrating particles from the source, a positioning apparatus configured to position the source relative to the object and the detector, and an imaging system coupled to the source, the detector, and the positioning apparatus. The imaging system may be configured to control the positioning apparatus to position the source and detector relative to the object, control the source and the detector to acquire the series of projection images, and construct a tomographic volume capable of exhibiting super-resolution morphology and contrast-enhancement arising from injection of an exogenous contrast agent from data representing the acquired series of projection images or a subset thereof.

Further aspects of the invention include a contrast-enhanced digital tomosynthesis method for imaging an object. The method may include positioning at least one source of penetrating particles relative to at least one detector and the object, the at least one detector having an array of pixels, and acquiring a series of images. The method may also include constructing at least one tomographic volume capable of exhibiting super-resolution morphology and contrast-enhancement arising from injection of an exogenous contrast agent from data representing the acquired series of projection images or a subset thereof.

Additional aspects of the invention include a contrast-enhanced digital tomosynthesis method for obtaining four dimensional image data. The method includes injecting a contrast agent into the blood stream of a patient, acquiring a series of images of the patient over a plurality of different angles, where one image is acquired at each angle, and constructing four dimensional image data for the patient from the acquired series of images.

BRIEF DESCRIPTION OF THE DRAWINGS

The invention is best understood from the following detailed description when read in connection with the accompanying drawings, with like elements having the same reference numerals. This emphasizes that according to common practice, the various features of the drawings are not drawn to scale. On the contrary, the dimensions of the various features are arbitrarily expanded or reduced for clarity. Included in the drawings are the following figures.

DETAILED DESCRIPTION OF THE INVENTION

Aspects of the invention enable dose-reduced four-dimensional contrast enhanced tomosynthesis. Embodiments combine the merits of tomosynthesis and MRI (anatomical data, such as breast imaging, chest imaging, musculo-skeletal imaging, etc., and perfusion data) to achieve dynamic four-dimensional (4D) contrast-enhanced tomosynthesis. 4D imaging involves acquisition of 3D images over time. By looking at the movement of the contrast agent, blood flow through a 3D volume can be visualized.

Typical PET/CT, MR/CT, x-ray/MR, etc., imaging processes require registration between modalities upon which a patient is being imaged. The systems, methods, and devices disclosed herein provide contrast-enhanced tomosynthesis imaging without requiring registration between modalities. Generally, data for tomosynthesis imaging utilized for producing images and/or rendering of an object/patient being imaged is acquired simultaneously according to aspects of the invention, such that registration between modalities is not required.

Figure 1:
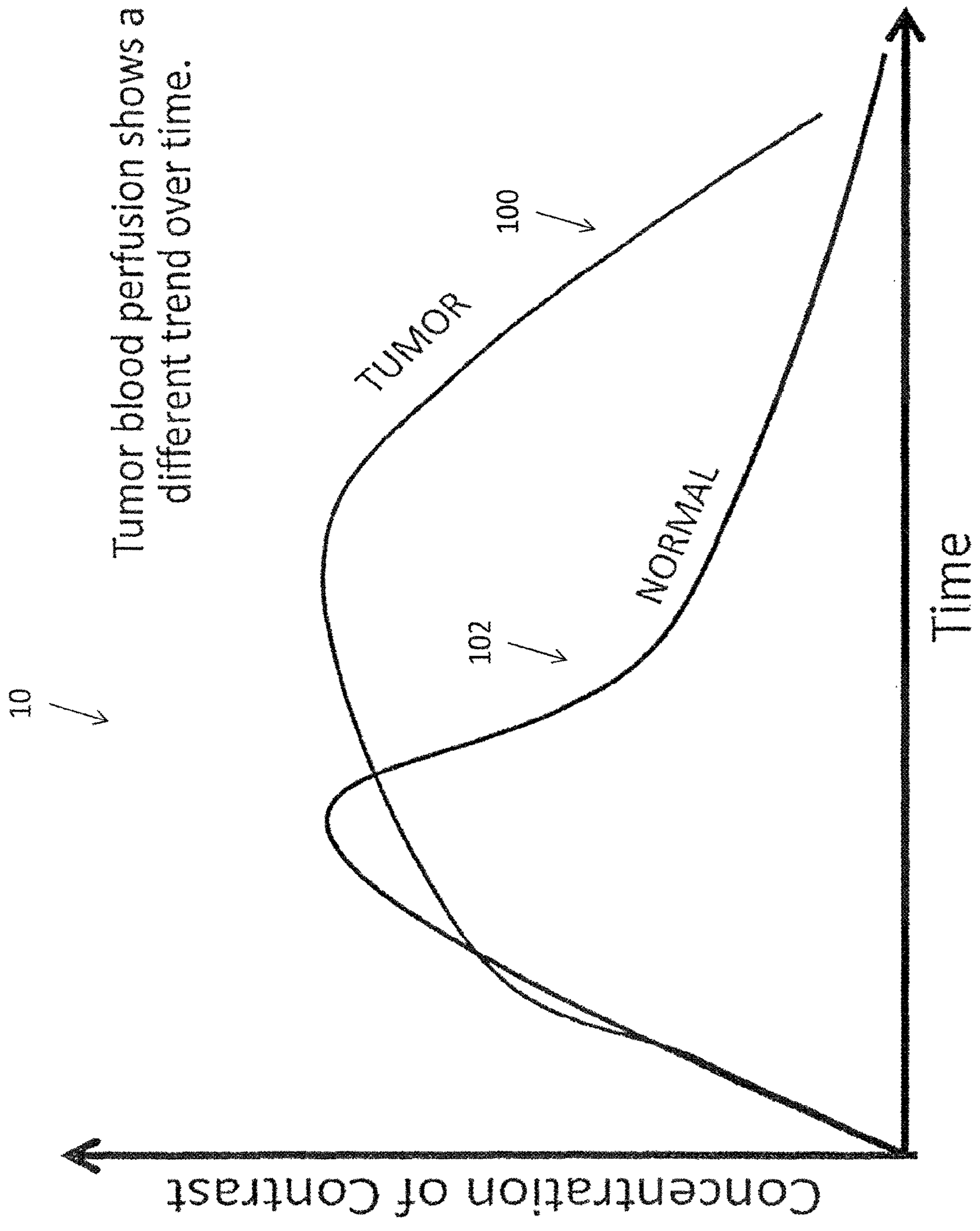
FIG. 1 is a graph depicting movement of contrast agents through normal and cancerous tissue.

Perfusion data can help draw conclusions about abnormal angiogenesis, which is a well-characterized precursor to tumor development as shown in FIG. 1. FIG. 1 is a graph 10 that depicts the change in concentration of contrast of an image over time in contrast-enhanced tomosynthesis imaging (CETI). Perfusion data indicative of the presence of a tumor results in a different trend of the contrast concentration over time, as shown by line 100, versus perfusion data indicative of normal results (e.g., no presence of a tumor), as shown by line 102.

Obtaining 4D data simply by acquiring a series of 3D tomosynthesis reconstructions at different time-points, however, would greatly increase the radiation dosage to the patient. As used herein, those of skill in the art will understand reference to the object being imaged may include any object, patient, particular anatomy of a patient, etc., which may be imaged by the CETI systems, methods, and devices disclosed herein. In accordance with the invention, instead of acquiring a full set of projections at each time-point, fewer images are acquired (e.g., one single-energy or dual-energy projection (e.g., a pair of projections made at two different energies or a single projection made with a detector capable of resolving the projection data into two or more energy bins) per time-point, with each projection acquired at a different projection angle). A sliding window (e.g., a window function) may be applied over the projections to generate a series of reconstructions. Windowing produces a moving average of the original data along two dimensions—time and angle, and results in a 4D reconstruction in which the 3 spatial dimensions and the 4th time dimension can be fully interrogated.

FIGS. 2A-2D depict tomosynthesis systems 200, 202, 204, 206 in accordance with aspects of the invention. The system 200 at FIG. 2A includes a tube generator 20, a source 21 for emitting a beam 23 of particles (e.g., x-ray particles, neutrons, protons, particles of gamma, ultraviolet, visible, and/or infrared wavelengths, etc.), a filter 22 (e.g., a filter wheel adapted to select one of many filters), a stage 24 with object 26 being imaged, a detector 28, and a computer 29 that coordinates the other components of the system 200. Tomographic resolution may be achieved by motion of the object 26 being imaged, motion of the source 21, and/or a combination of motion of the object 26 and motion of the source 21. The tube generator 20, source 21 and the detector 28 may be generally configured for x-ray particle generation and x-ray projection detection as is described herein. It will be understood by one of skill in the art that the tube generator 20, source 21 and the detector 28 may be alternatively or additionally configured for generation and detection of additional or other particles that may be utilized for CETI. (e.g., neutrons, protons, etc.). The system 200 may be automated. The object 26 may be breast tissue or other tissue of an anatomy of a patient being imaged. In an embodiment, the object 26 is coupled to a contrast injection apparatus (not shown, but depicted as contrast injection 27 in FIGS. 2B-2D). The computer 29 may be positioned locally or remote to the other components.

Figure 2A:
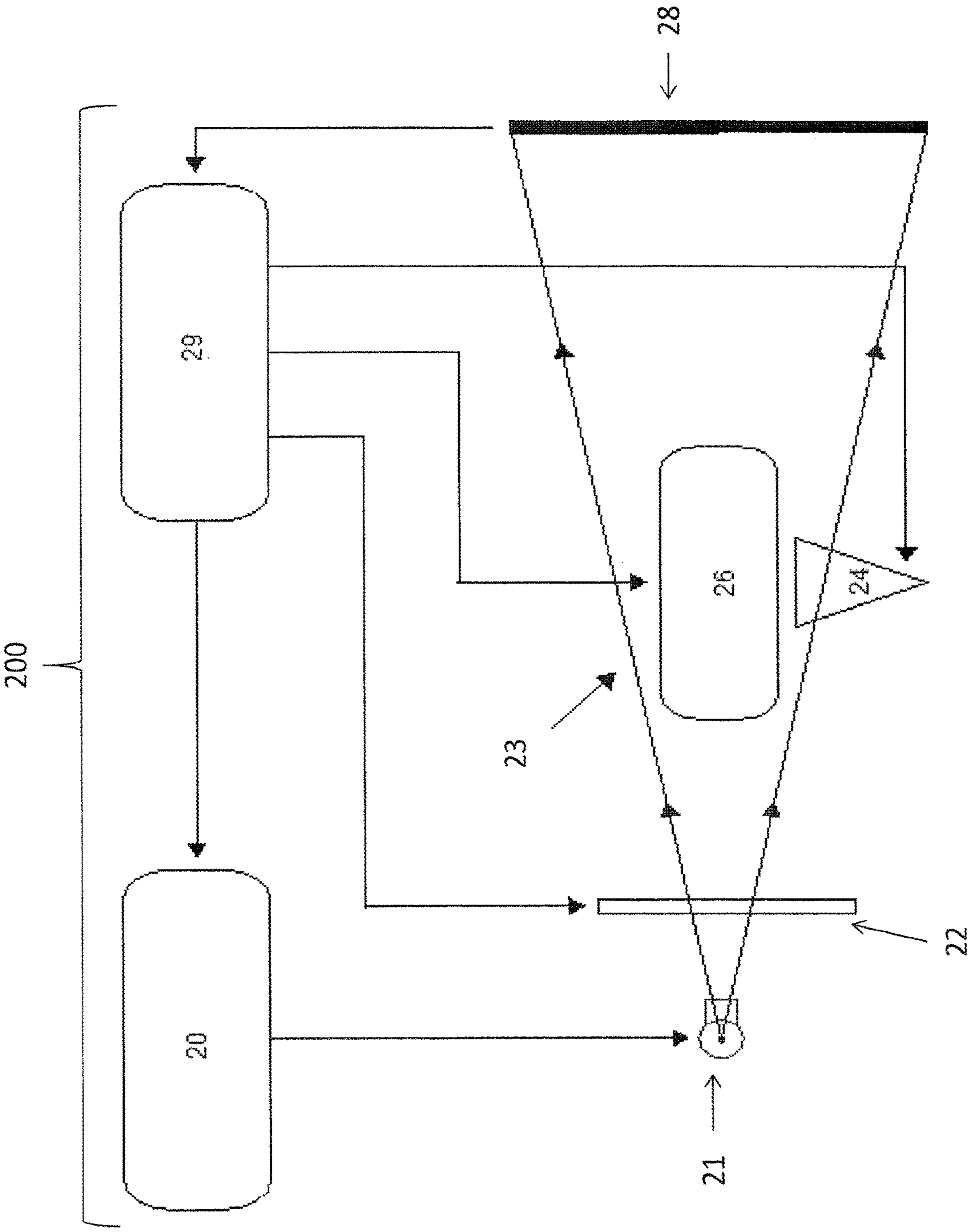
FIGS. 2A, 2B, 2C and 2D are block diagrams depicting systems for acquiring 4D image data in accordance with aspects of the invention.
Figure 2B:
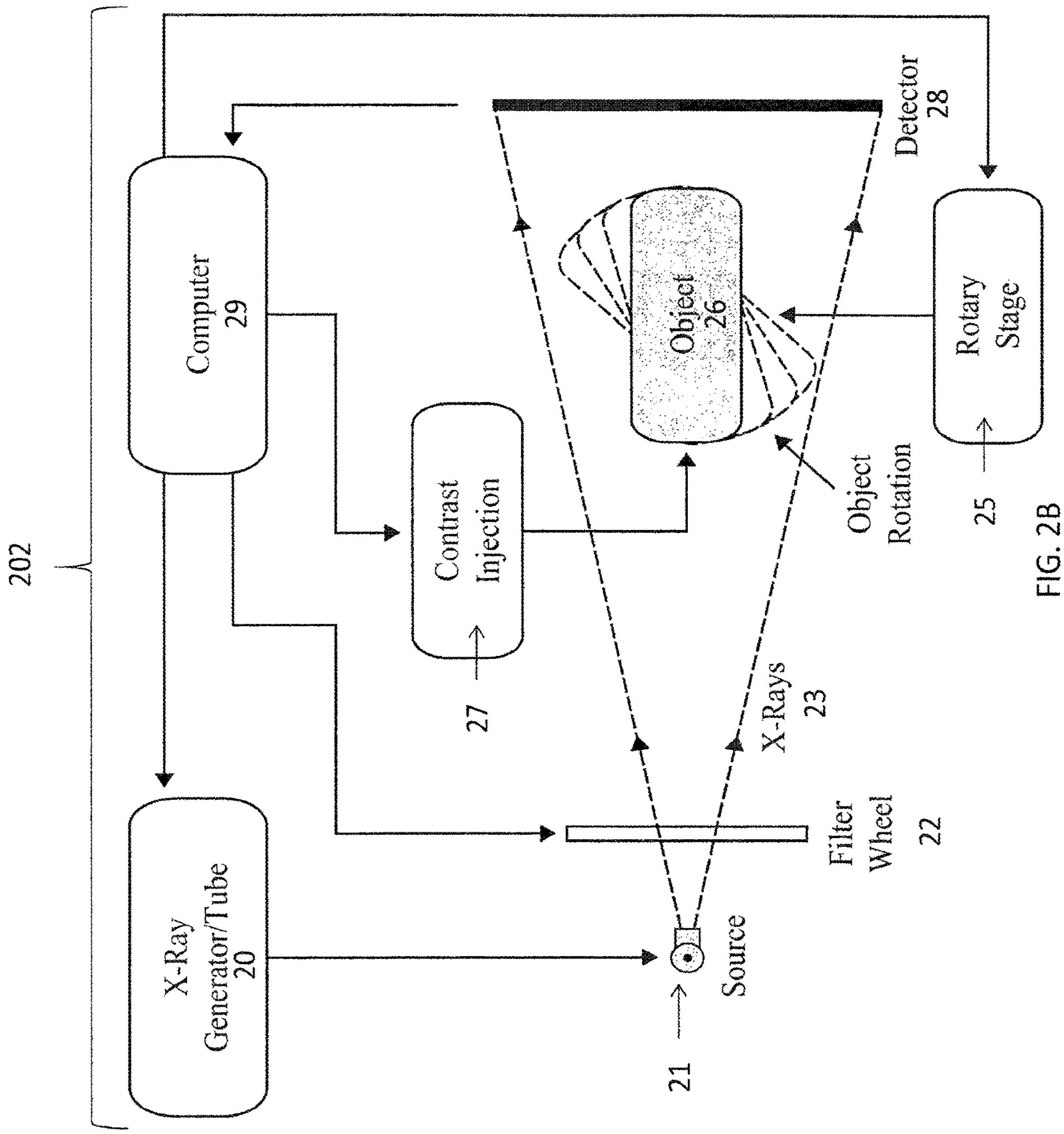
Figure 2C:
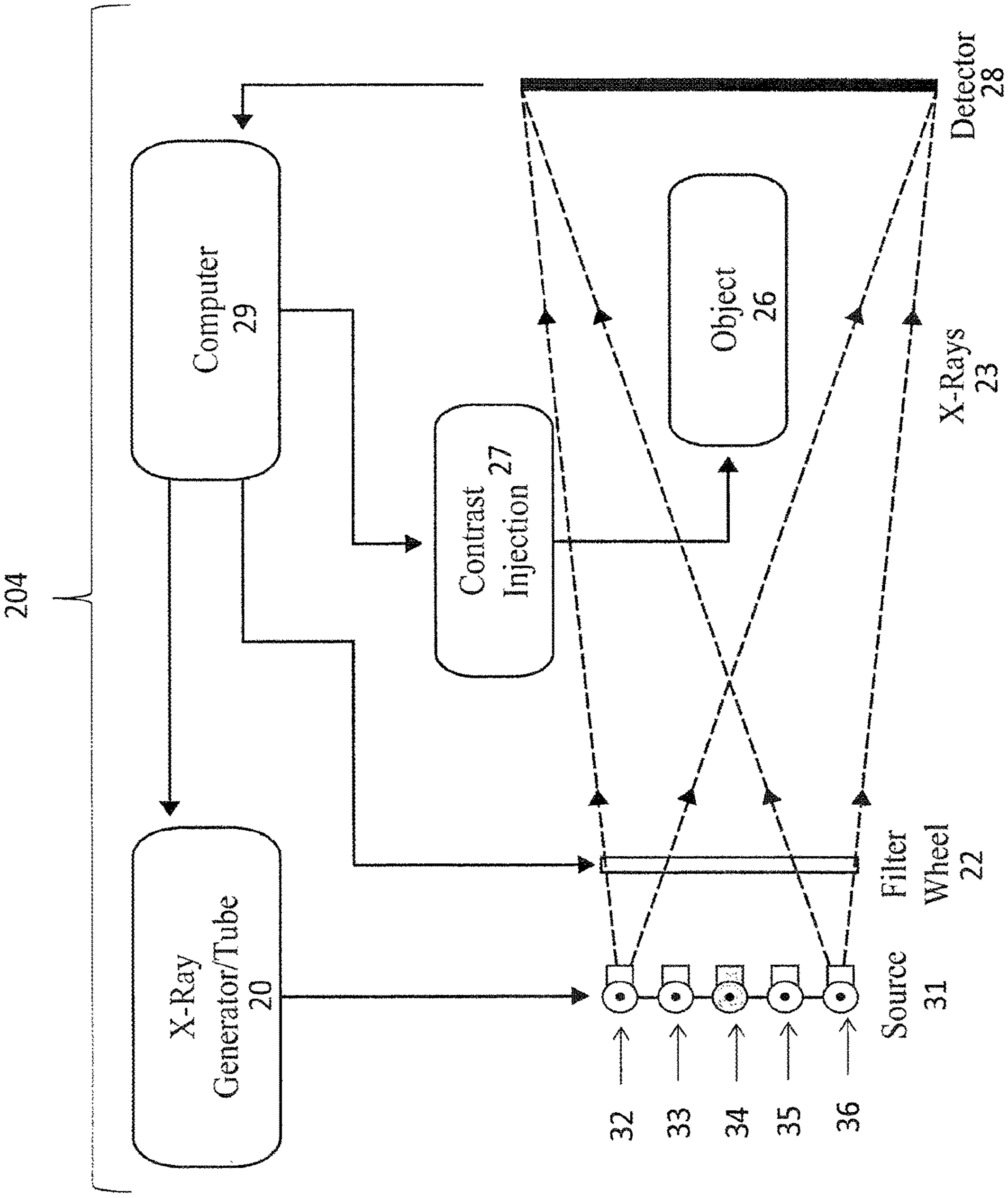
Figure 2D:
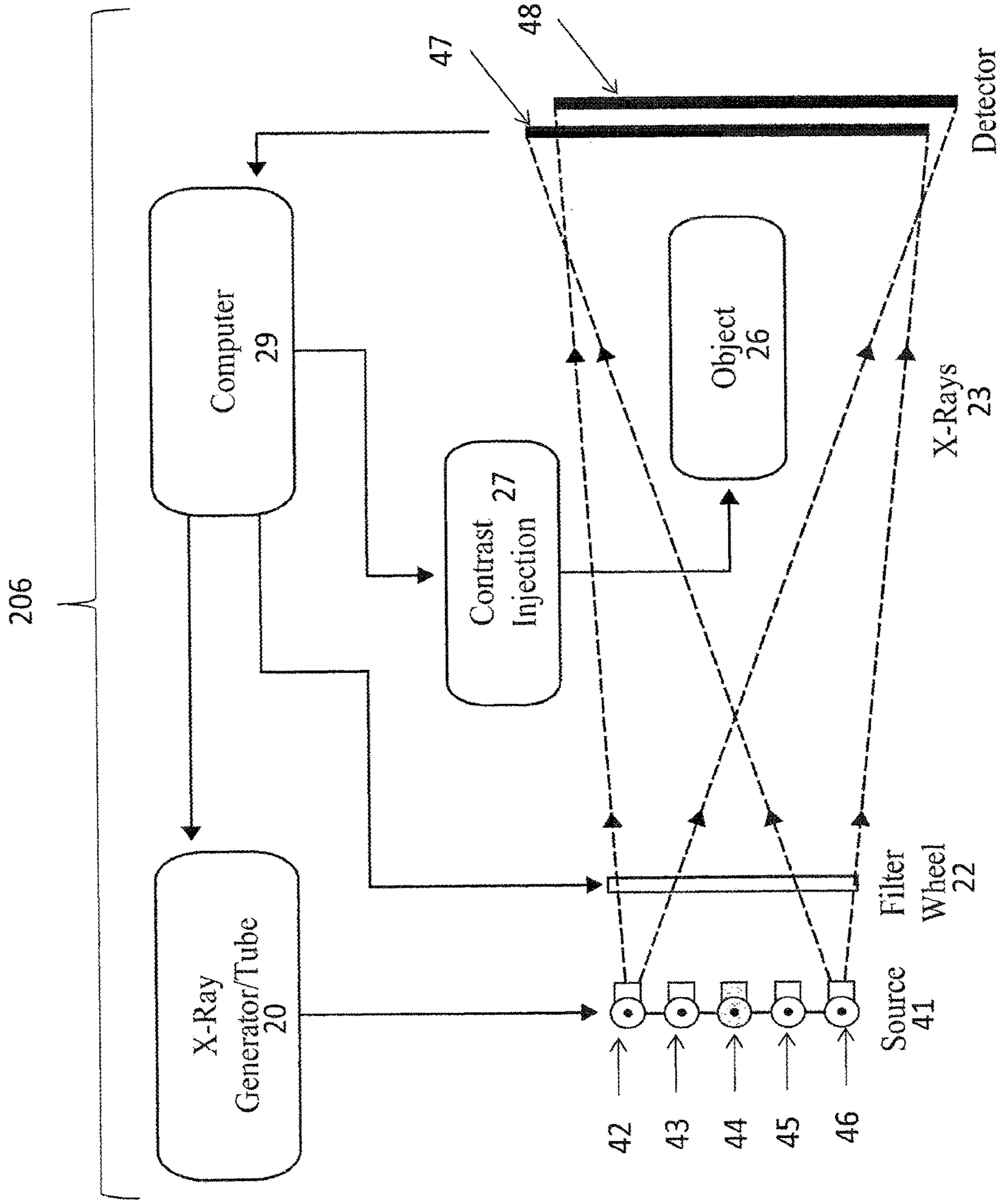

FIGS. 2B-2D depict systems 202, 204, 206 with different configurations in accordance with aspects of the invention. In the system 202 depicted FIG. 2B, the object 36 is coupled to (e.g., mounted to, attached to, etc.) a rotary stage 25. The rotary stage 25 is configured to rotate the object 26 along predetermined arcs such that the source 21 emits radiation (x-rays 23) to the object 26 at various angles, providing multiple projections that are detected by the detector 28 for 4D CETI. At FIG. 2C, the system 204 includes a source 31 that is made up of multiple emitters 32, 33, 34, 35, 36. The emitters 32-36 are fixed at various positions with respect to the object 26, such that multiple projections of the object 26 are produced at various angles that are detected by the detector 28 for 4D CETI. The system 206 shown at FIG. 2D has a source 41 that includes multiple emitters 42, 43, 44, 45, 46, and the detector includes a first detector 47 and a second detector 48. The first detector 47 is offset at a distance and an angle with respect to the second detector 48, such that each detector 47, 48 detects projections of the object 26 at various angles. In each of the systems 200, 202, 204, 206, the detectors 28, 47, 48, the sources 21, 31, 41, emitters 32-36, 42-46, tubes 20, and/or objects 26 may be fixed, configured to move, or both. It will be understood to those of skill in the art that multiple sources and multiple detectors may refer to multiple unique sources and detector, or equally can refer to multiple source positions and multiple detector positions achieved through moving the source or detector to these positions. Although the configurations of systems 200, 202, 204 and 206 are depicted independent of each other, one of skill in the art will understand from the disclosure herein that any combination of the features of systems 200, 202, 204 and 206 may be utilized for CETI in accordance with the invention.

A contrast agent is injected into the blood stream of a patient in accordance with aspects of the invention. The contrast agent may be an exogenous contrast agent such as an Iodine-based contrast agent (e.g., a commercial iodinated contrast agent, which typically have a large molecular structure that encompasses 1 to 6 iodine atoms).

Figure 3:
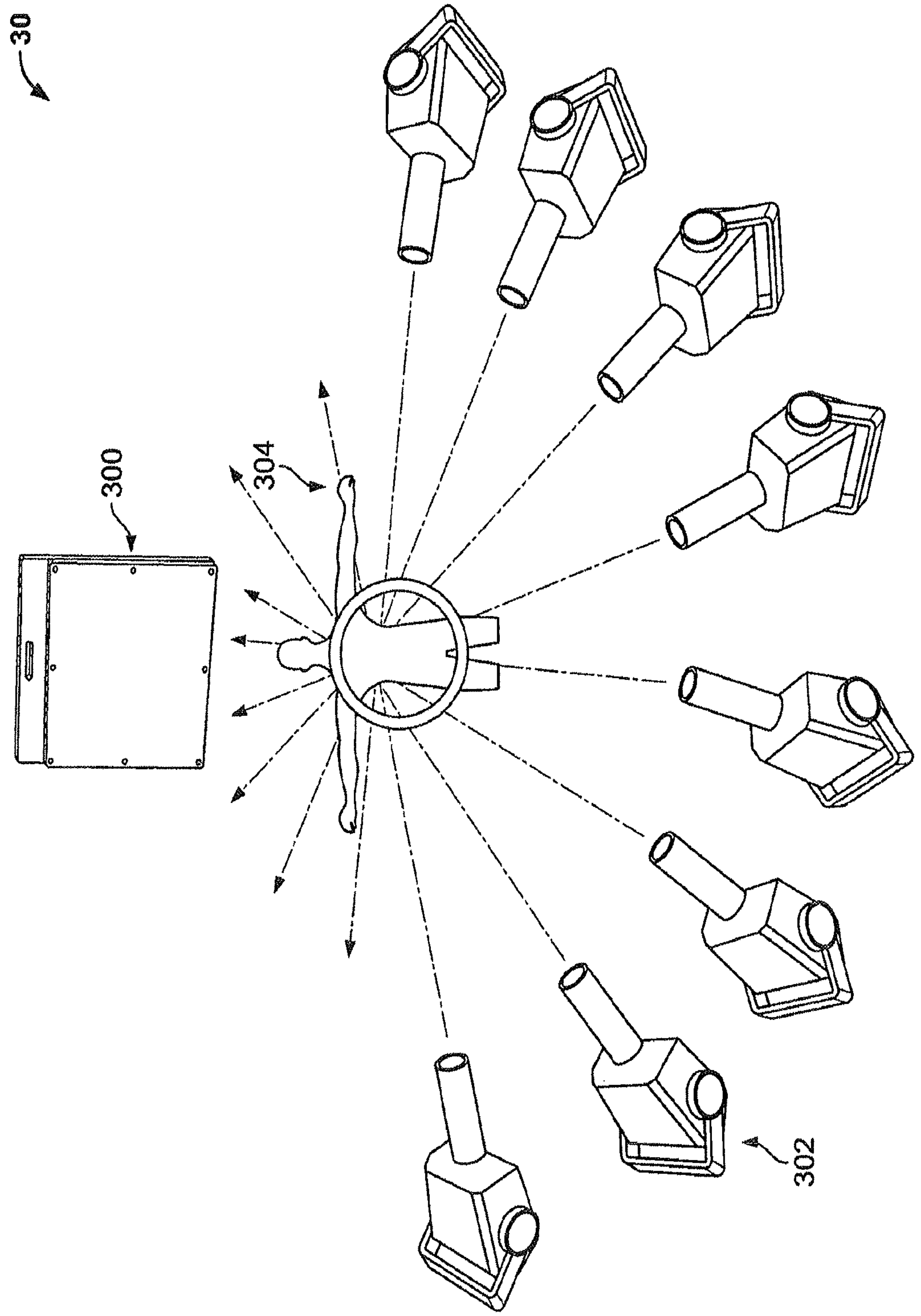
FIG. 3 is an illustration depicting an imaging system according to aspects of the invention.

FIG. 3 depicts an imaging system according to aspects of the invention. The system 30 includes an X-ray detector 300, an x-ray tube 302 (e.g., a device to emit penetrating particles such as x-ray radiation), and a patient 304 positioned such that the x-ray detector 300 may detect the emissions transmitted from the tube 302 to the patient 304. FIG. 3 depicts the tube 302 in various positions relative to the patient 304. At each position, a unique image of the patient 304 may be captured and processed via the x-ray detector 300. In an embodiment, the x-ray tube 302 is adapted to move between the various positions depicted in FIG. 3. In one embodiment, the system 30 includes a plurality of x-ray tubes fixed at various locations relative to the patient 304. In addition, multiple x-ray tubes may be fixed in position, while the object being imaged is rotated with respect to the x-ray tubes and detector(s). For example, one or more x-ray sources may be combined with one or more stationary detectors, one or more stationary x-ray sources may be combined with one or more moving detectors, one or more moving x-ray sources may be combined with one or more moving detectors, multiple fixed electronically switched x-ray sources may be combined with one or more electronically switched detectors, one or more fixed x-ray sources may be combined with one or more fixed detectors combined with a translation and/or rotation stage to move the target, etc. It is contemplated that a combination of x-ray tubes/sources adapted for movement relative to the patient 304 and x-ray tubes/sources fixed at positions relative to the patient 304, as well as additional detectors, fixed and/or adapted to move, positioned accordingly for multiple tubes/sources may be utilized for tomosynthesis imaging of a patient.

Figure 4A:
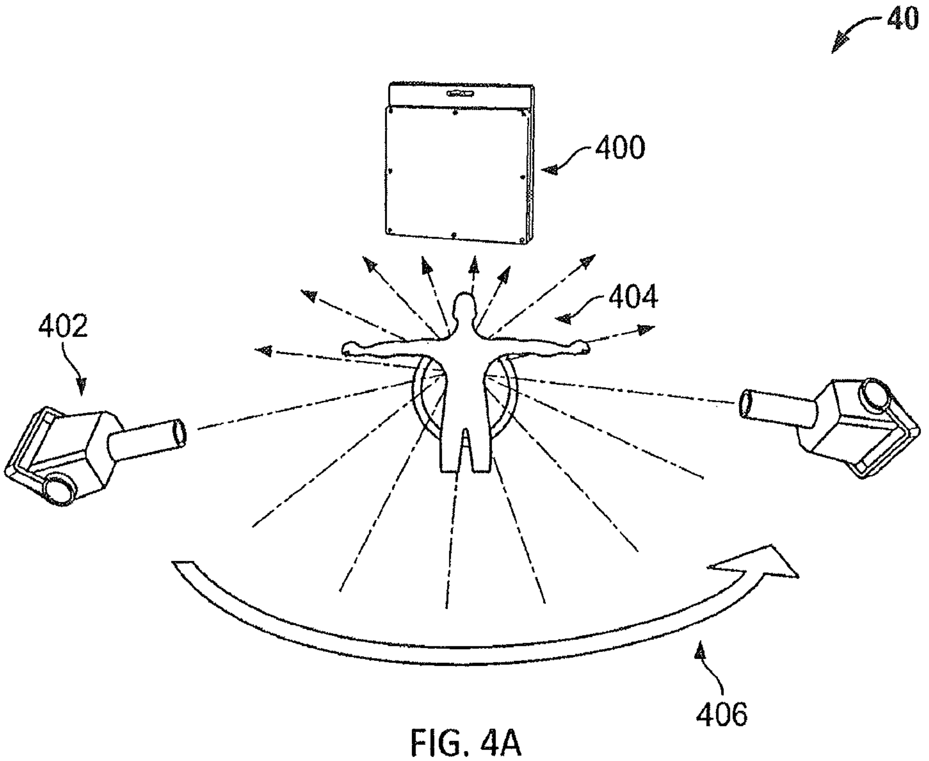
FIGS. 4A, 4B and 5 are illustrations depicting imaging of a patient in accordance with aspects of the invention.
Figure 4B:
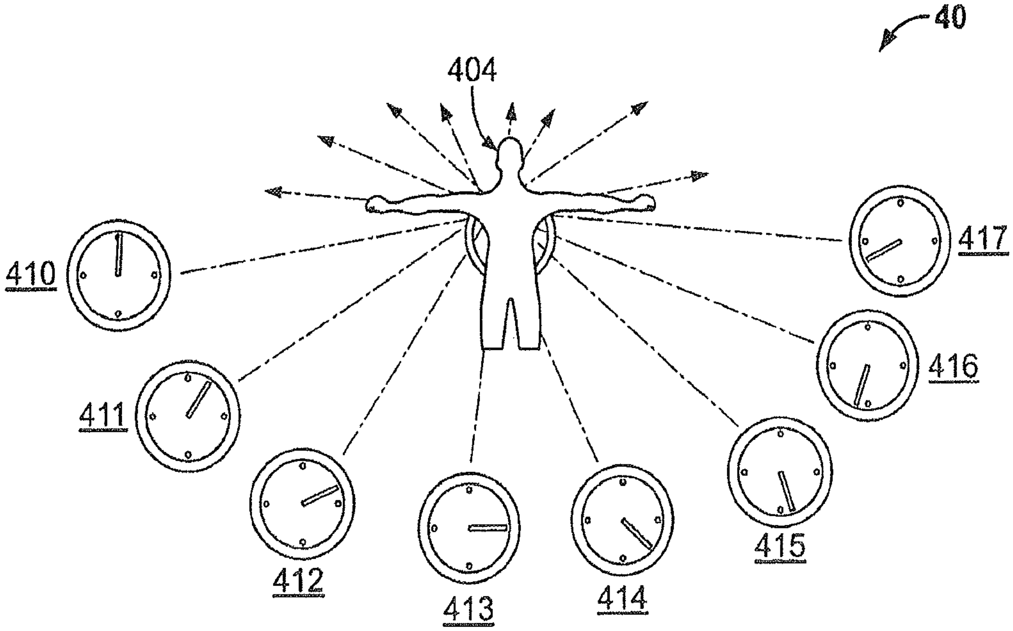
Figure 5:
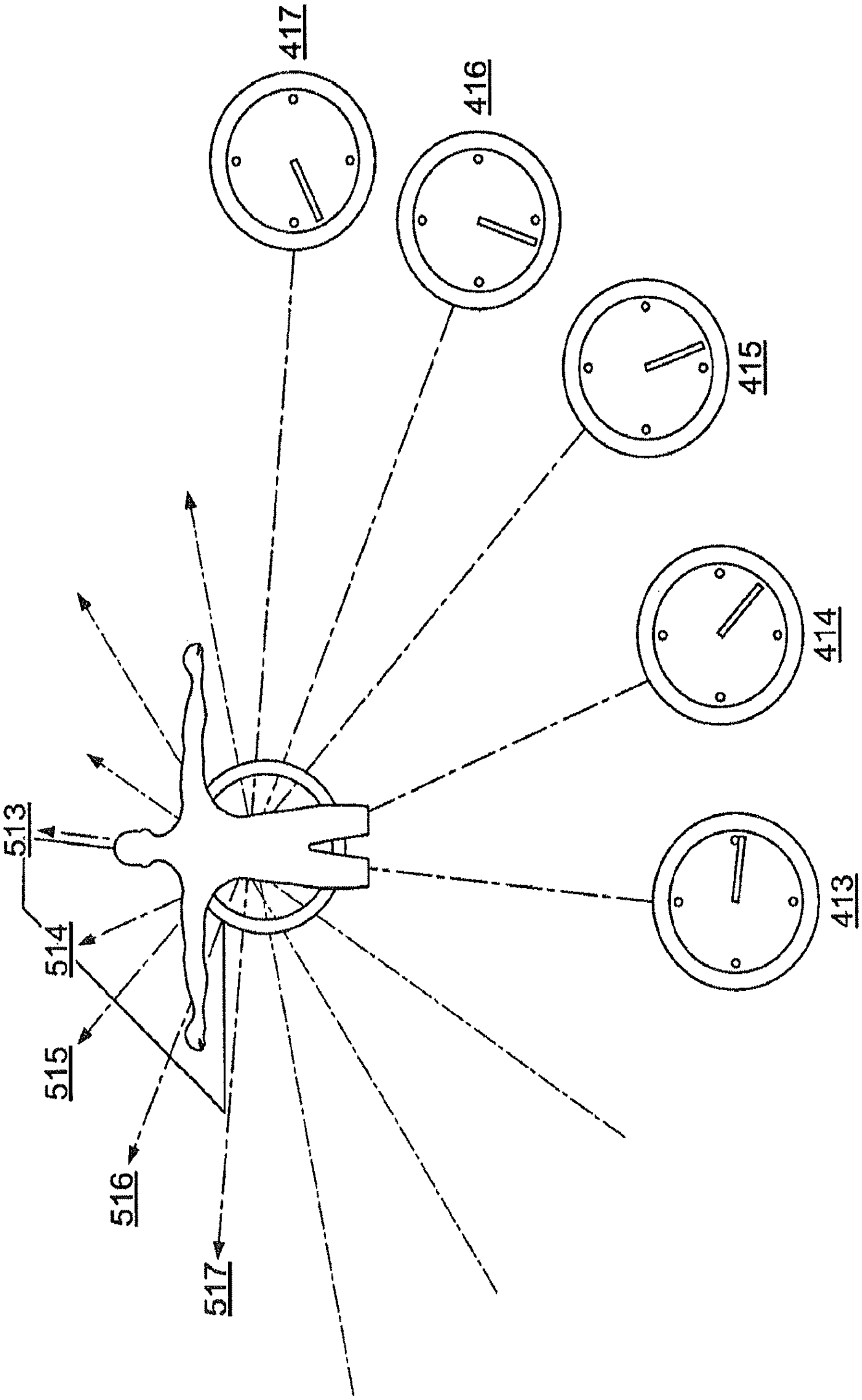
Figure 6A:
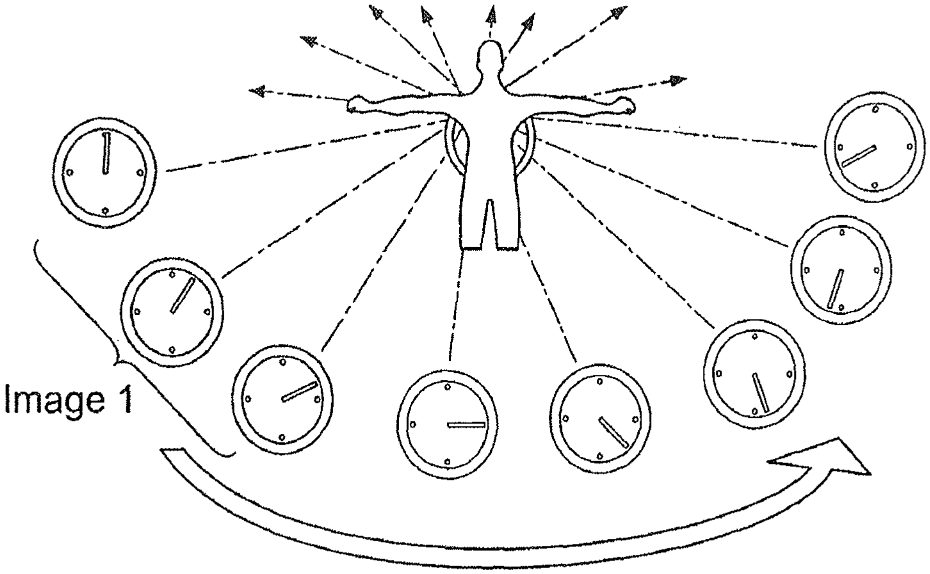
FIGS. 6A, 6B, 7A, 7B, 7C, and 7D are illustrations depicting the reconstructions of 4D image data in accordance with aspects of the invention.
Figure 6B:
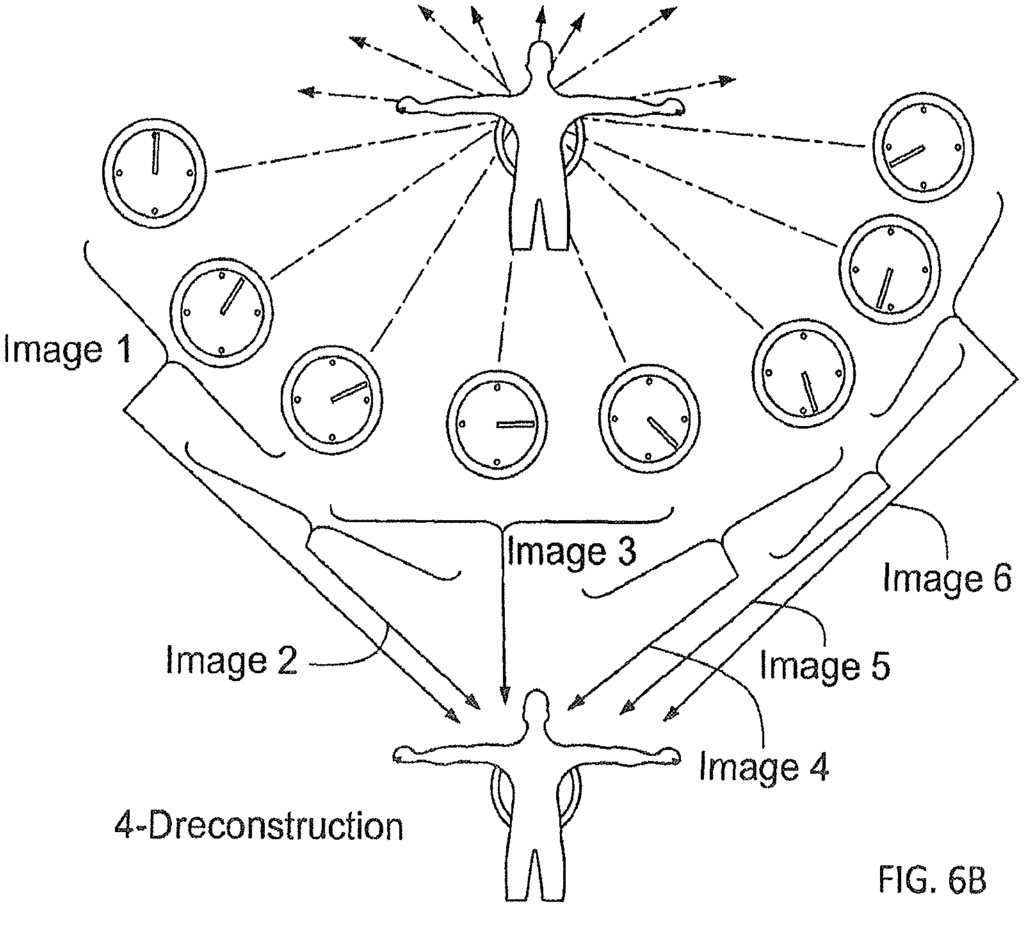

Referring next to FIGS. 4A, 4B and 5, a tomosynthesis system 40 according to aspects of the invention is depicted. The system 40 includes an x-ray detector 400 and an x-ray 402 tube configured for tomosynthesis imaging of a patient 404. FIG. 4A depicts a single x-ray tube 402 that is adapted to move in a semi-circular direction (shown as an arc 406) with respect to the patient 404 and/or the detector 402. One of skill in the art will understand that the x-ray tube 402 may be adapted to move in both the clockwise and counterclockwise directions, and may also be configured to move in a full 360 degree rotation with respect to the patient 404. Additionally, the tube(s) 402 may also be configured for movement/placement across various families of motion (e.g., linear motion, motion on a curved path, random motion, and motion; see, for example, U.S. Pat. No. 8,233,690) coordinate systems and various lengths/dimensions for CETI of a patient (e.g., axes along a Cartesian coordinate system; radial, theta and phi axes along a spherical coordinate system; radial and theta axes along a polar coordinate system; radial, phi, and azimuthal axes along a cylindrical coordinate system, etc.).

FIG. 4B depicts various positions (410-417) at which the x-ray tube 402 may be configured to emit x-ray radiation for detection and image capture via the detector 400. Although eight positions (410-417) are depicted, it will be understood to one of skill in the art that less or more positions may be used from the disclosure herein. In an embodiment, the positions (410-417) at which the x-ray tube 402 is adapted to emit x-ray radiation are dependent upon a predetermined time interval (e.g., every 5 seconds). The time intervals may be determined based upon the timing of the motion under consideration (e.g., the time course over which the tumor fills with the contrast agent), the window needed to achieve minimally sufficient 3D image quality (e.g., when five projections are used at 5 seconds per projection, the minimum window width would be 25 seconds (five times 5), which is acceptable for a phenomenon with a one minute peak), etc.

At FIG. 5, positions 413-417 are depicted in greater detail. At each position, a projection is captured via emission of x-ray radiation from the tube 402 and detection by the detector 400. At position 413, the projection 513 is captured by the detector 400 and is associated with the time at which the tube 402 is located at position 413.

The process is repeated for position 414 and projection 514, position 415 and projection 515, position 416 and projection 516, and position 417 and projection 517. Each projection 513-517 detected by the x-ray detector 400 is rendered into an image that is unique relative to one another, and each image is associated with a position of the x-ray tube 402 and/or the time associated with the position of the x-ray tube 402, and the data is interpolated for reconstruction. FIGS. 4A-5 illustrate that projections (e.g., projections 513-517) are acquired at different angles within a limited angular range around the object 26 (FIG. 2) (e.g., patient 304/404), but that each projection is acquired at a different time point.

FIGS. 6A-7D depict examples of the reconstruction process according to aspects of the invention. At FIGS. 6A and 6B, subsets of these projections (indicated by "image 1," "image 2/" "image 3," "image 4," "image 5," and "image 6") can be used to generate reconstructions. FIG. 66 illustrates eight projections with reconstructions ("image 1"-"image 6") formed from three of the projections. It is contemplated that more or fewer projections/reconstructions may be employed.

In another example as illustrated in FIGS. 7A-7D, it is not necessary for projections forming a reconstruction to be from the same cycle of projections. FIGS. 7A-7D depict a first cycle of projections 700, a second cycle of projections 702 and a third cycle of projections 704. Each cycle 700, 702, and 704 employs an x-ray tube configured to emit x-ray radiation at various positions relative to the patient according to a predetermined time interval. Although each cycle 700, 702 and 704 is shown to have eight positions, more or fewer positions may be utilized based on differing time intervals, angles/positions of the tube with respect to the patient, etc.

Figure 7A:
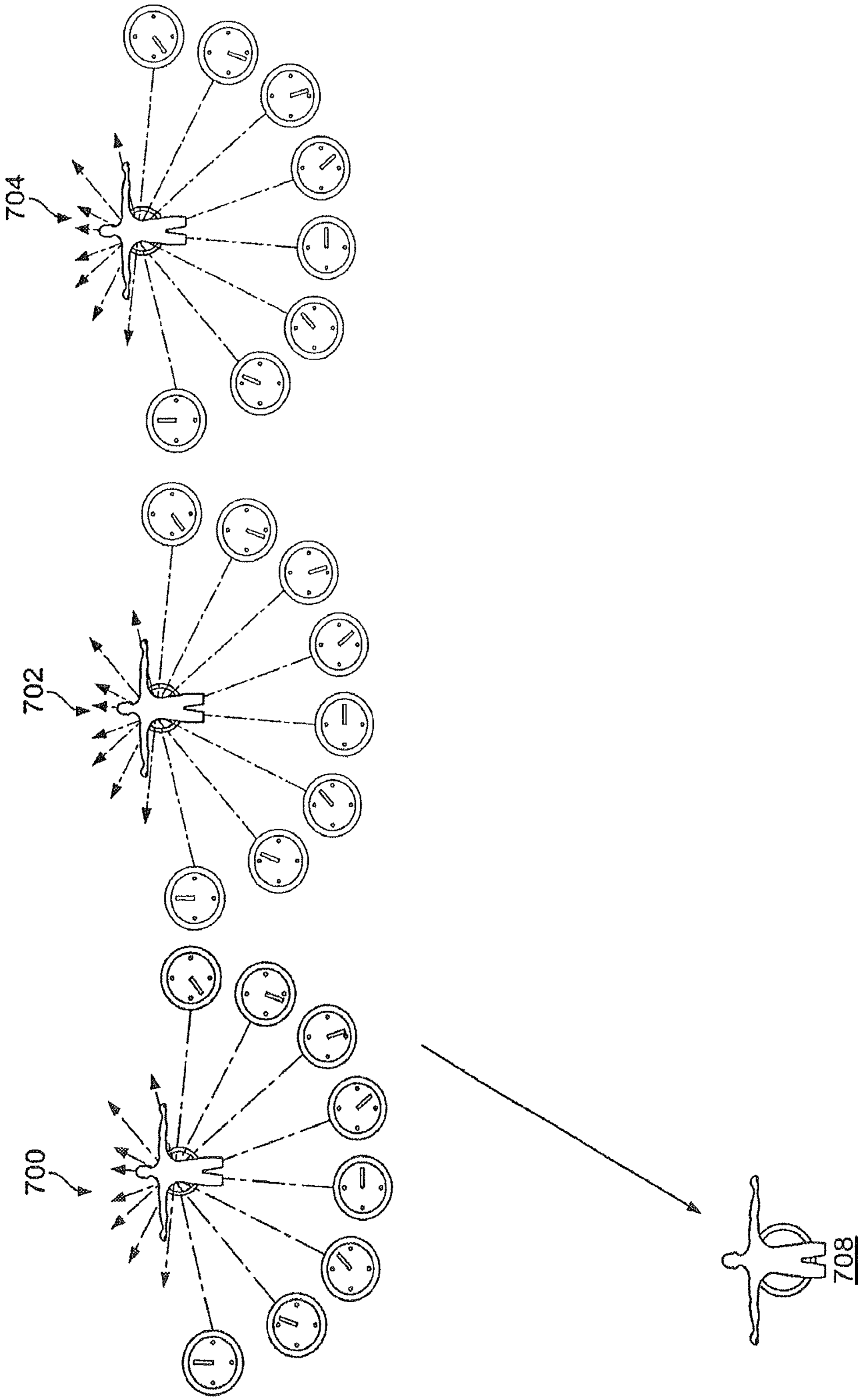
Figure 7B:
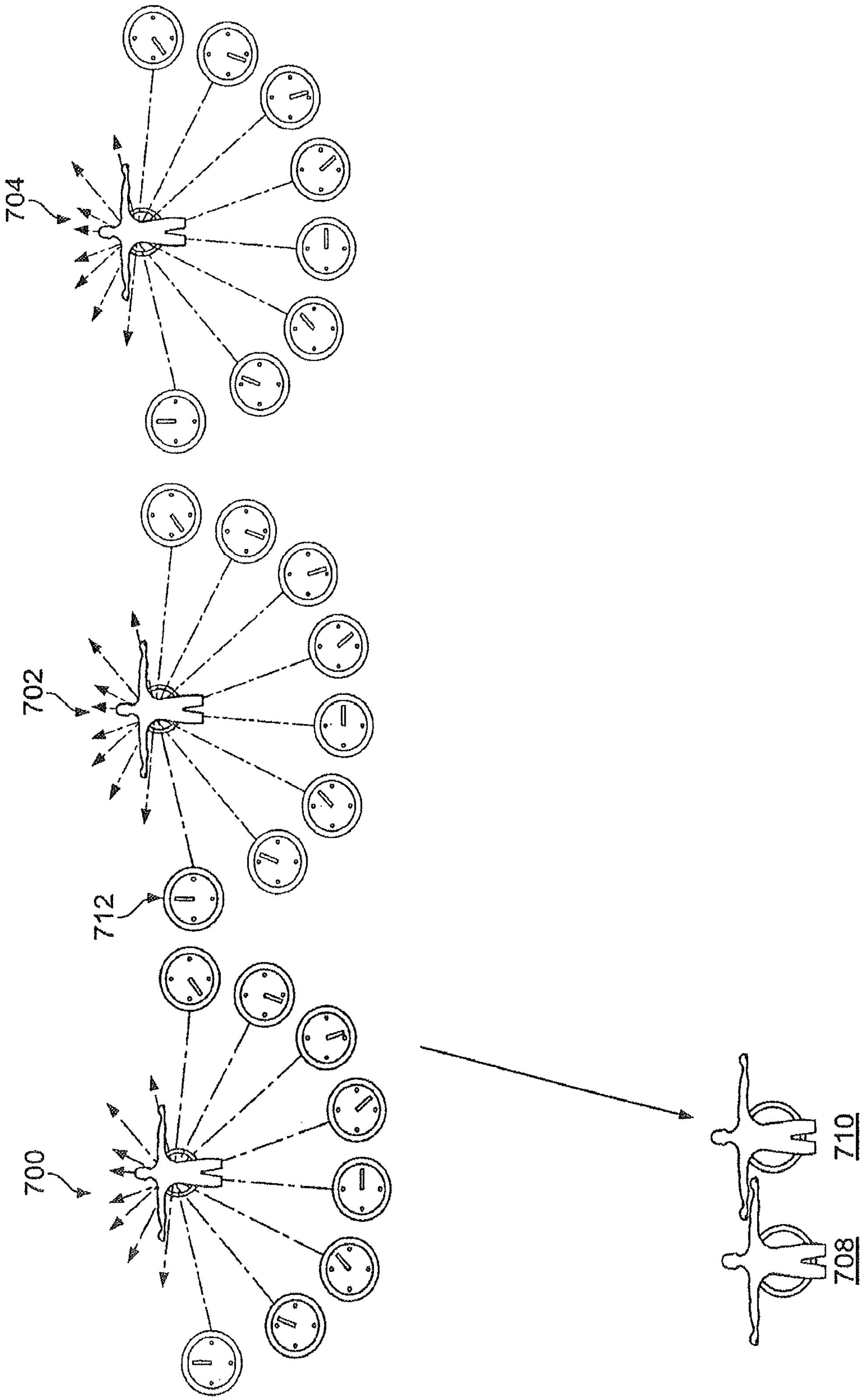
Figure 7C:
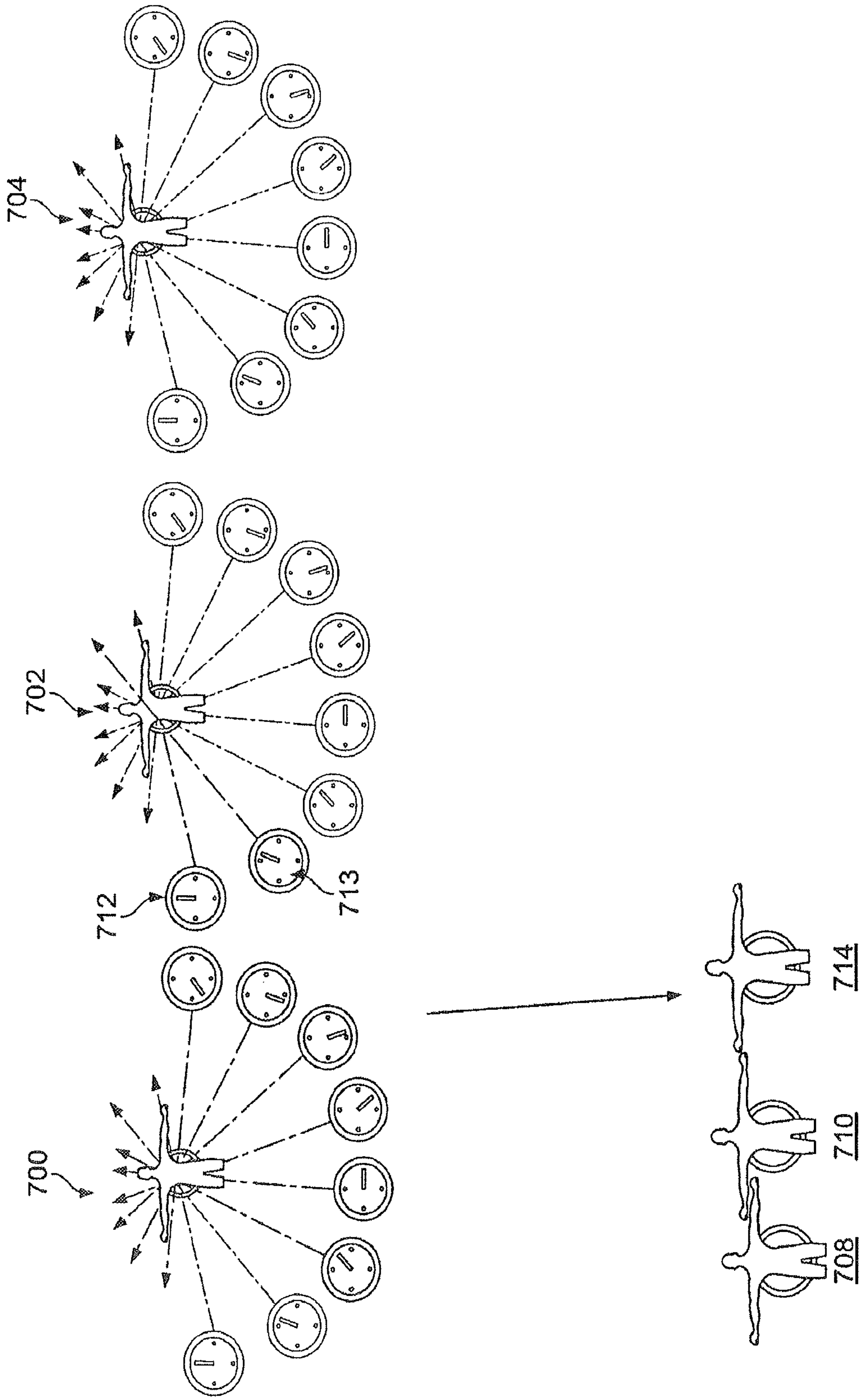
Figure 7D:
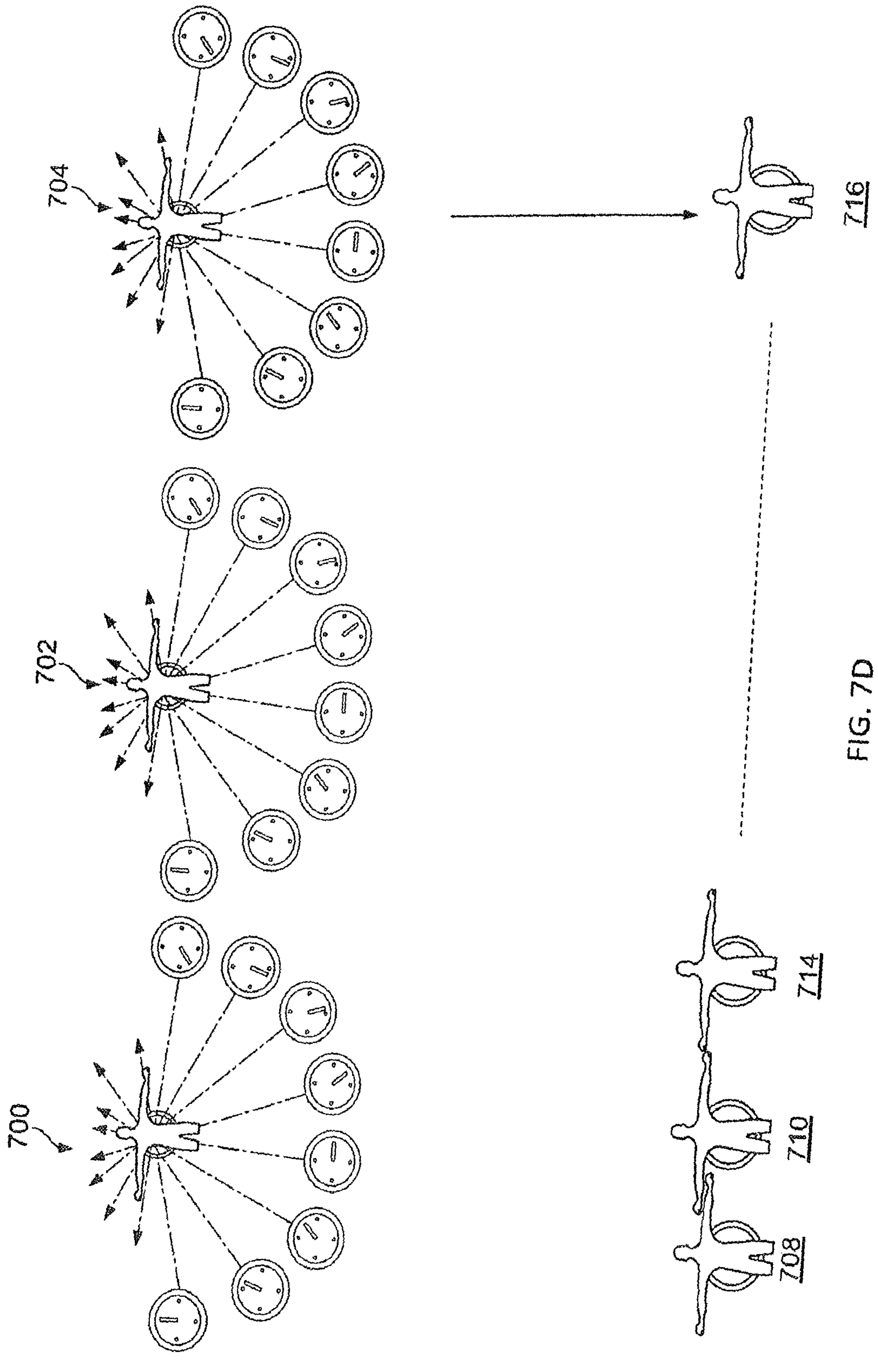

In FIG. 7A, a first reconstruction 708 is made from the eight projections in the first cycle 700. In FIG. 7B, a second reconstruction 710 is made from the last seven projections of the first cycle 700 and the first projection 712 of the second cycle 702. In FIG. 7C, a third reconstruction 714 is made from the last six projections of the first cycle 700 and the first two projections 712 and 713 of the second cycle 702. This reconstruction process may be repeated such that a final reconstruction 716 is made from the eight projections of the third cycle 704, as is shown in FIG. 7D.

Those of skill in the art will understand from the disclosure herein that various positions, angles, time intervals, projection combinations, cycles, etc., may be utilized for tomosynthesis reconstruction and imaging. For example, the time intervals between the positions of the x-ray tube(s) may be constant, or may not be constant. Various time intervals (e.g., a shorter time interval between a first position and a second position, and a longer time interval between a second position and a third position, etc.) may be utilized, and any number of positions may be selected for the CETI of the patient. Furthermore, in embodiments where cycles are utilized for CETI of the patient, each cycle may include the same number of projection or a different number of projections (e.g., a first cycle being constructed of five projections and a second cycle being constructed of seven projections, etc.). Each reconstruction may not necessarily be constructed in chronological order. Those of skill in the art will recognize from the disclosure herein that various positions, cycles, time intervals, chronological orders, cycles sizes, etc., may be utilized to conduct the CETI of the patient according to aspects of the invention. Additionally, it is not mandatory that projections be angularly adjacent to one another. It is also feasible to use multiple cycles to produce images with enhanced super-resolution. Enhanced super-resolution is achieved by offsetting the angles used in each cycle by small increments so that the range of angles is more finely sampled.

The capability to compute oblique reconstructions permits the usage of sets of projections that are not centered around the same angle to obtain reconstructions from the same viewing angle. Reconstruction software (such as RTT's (Real-Time Tomography, LLC of Villanova PA) Briona reconstruction software) provides dynamic real-time reconstructions that allow on-demand planar and oblique angle reconstructions, filtering updates and super-resolution magnified views. See, for example, U.S. Pat. No. 8,233,690.

Figure 8A:
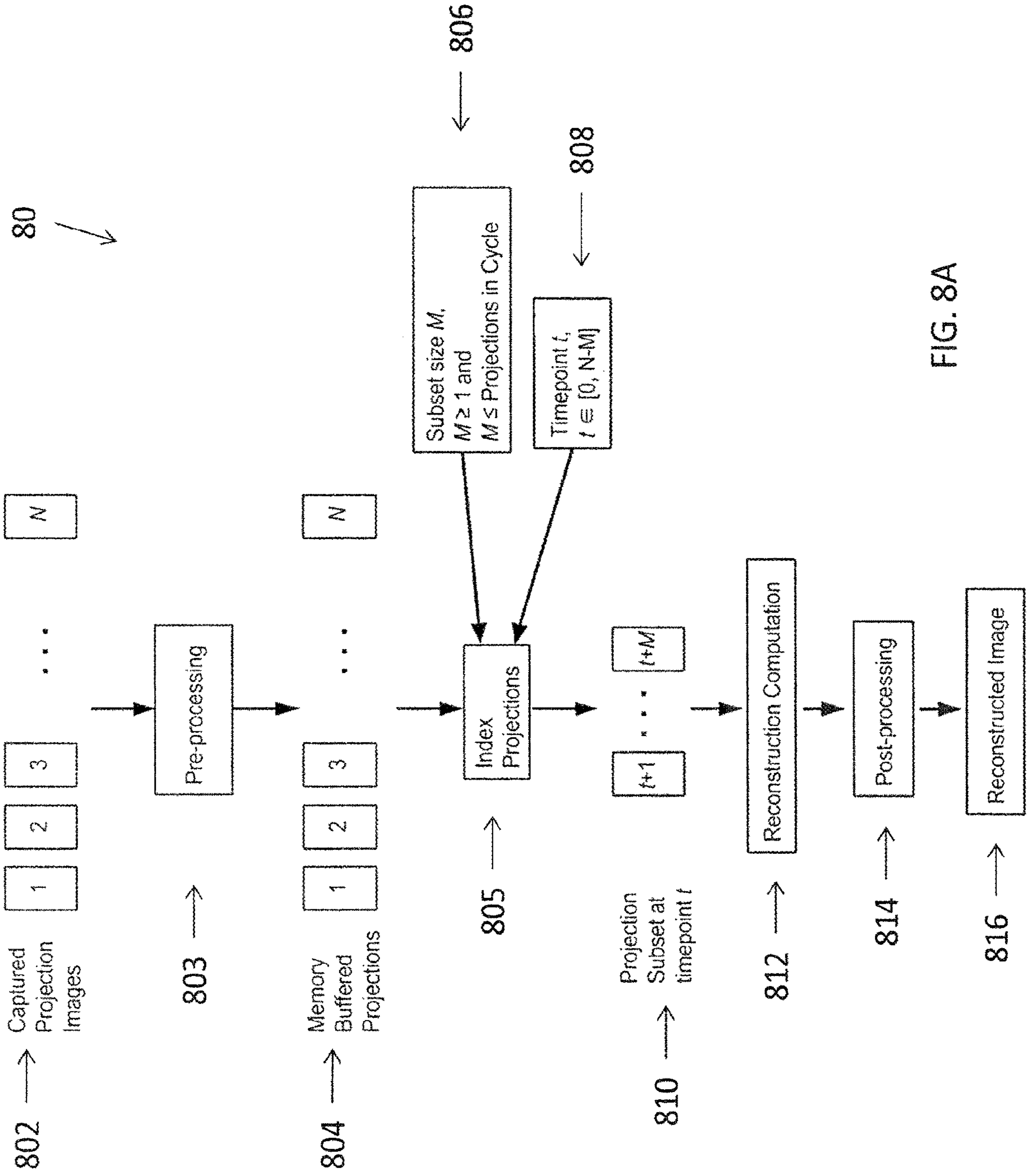
FIGS. 8A, 8B, and 8C are flowcharts showing steps for reconstruction processes according to aspects of the invention.
Figure 8B:
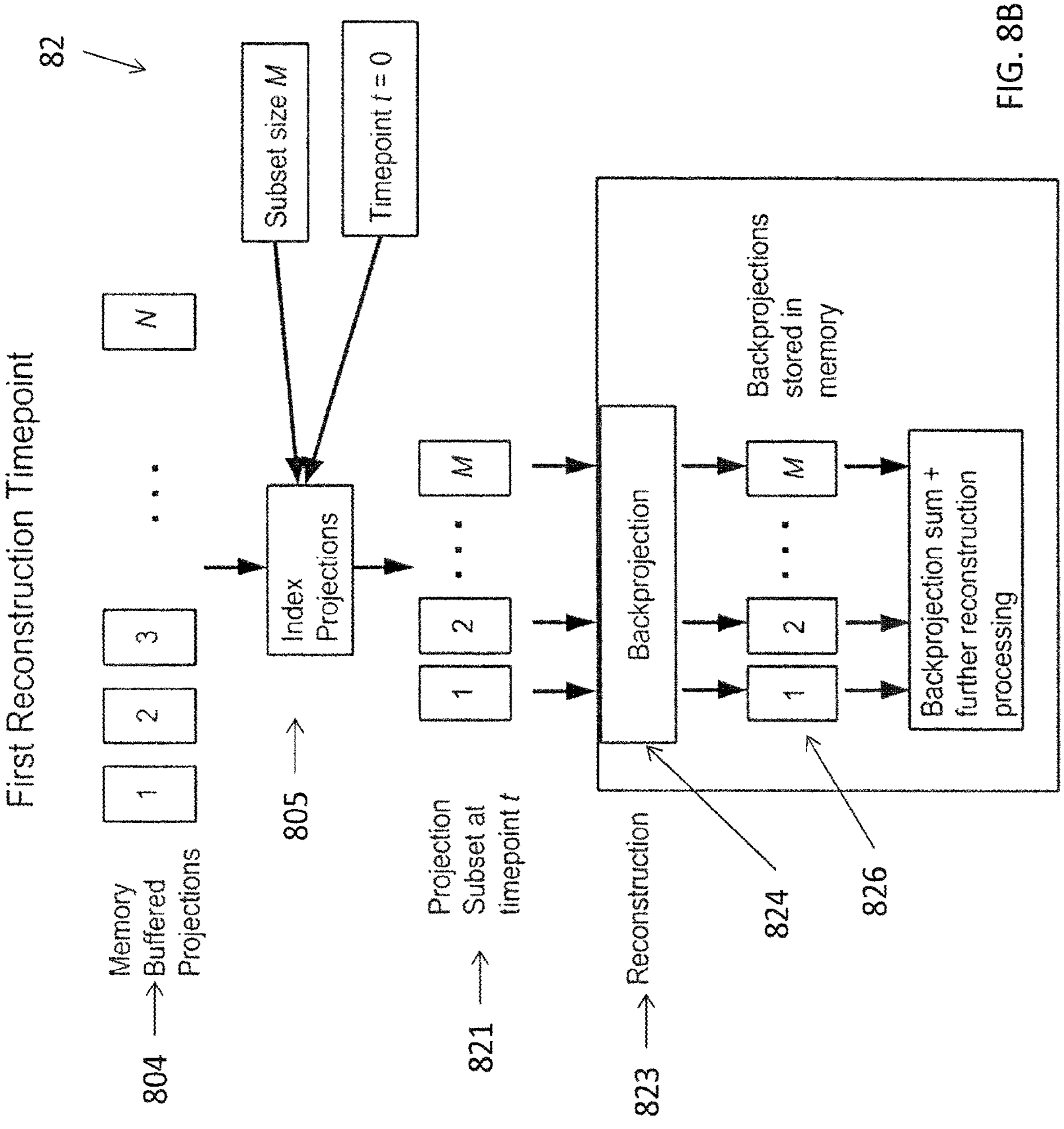
Figure 8C:
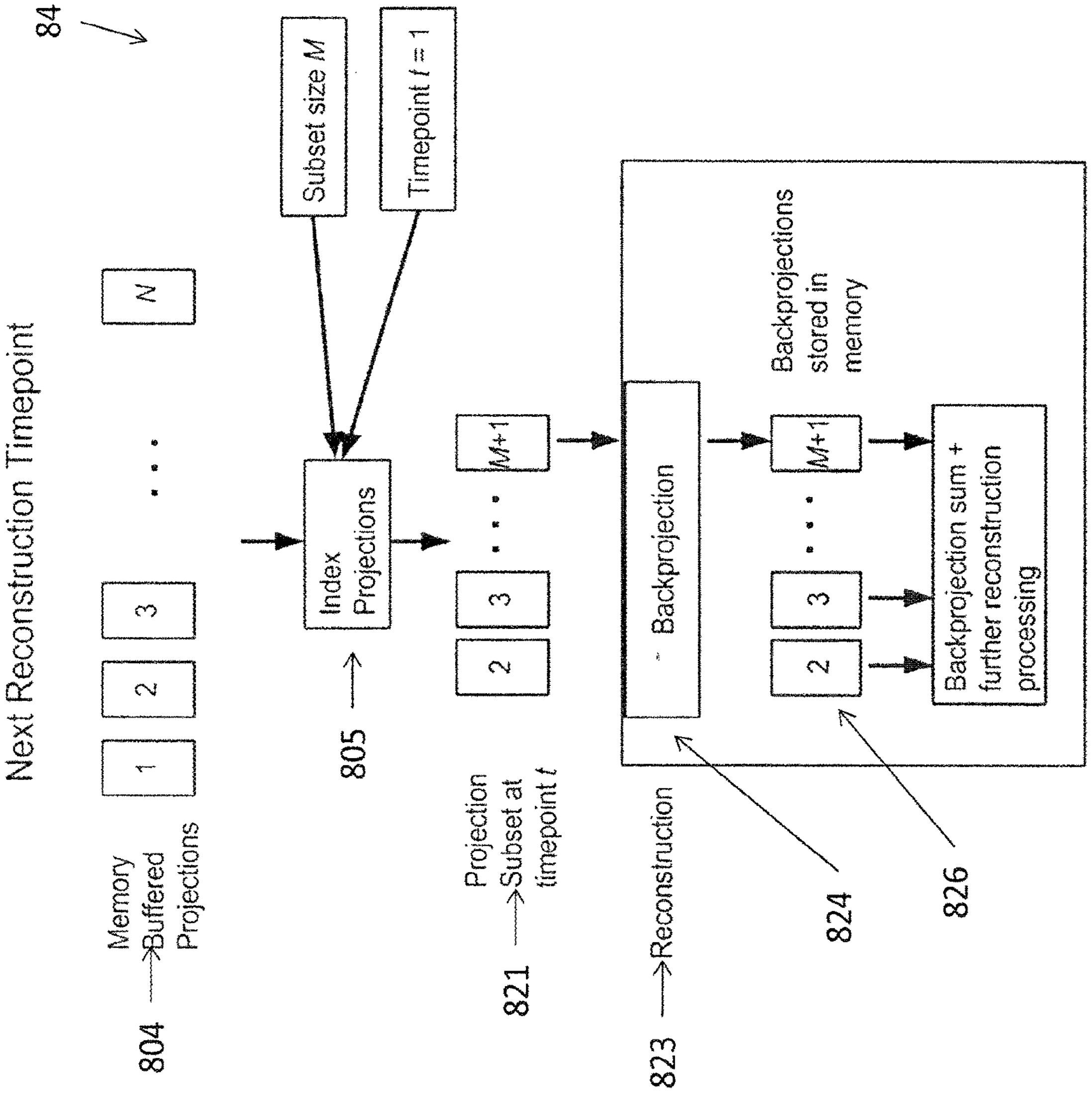

Additional improvements and features are added to the reconstruction software to provide reconstruction of 4D tomosynthesis datasets in accordance with aspects of the invention. Referring to FIGS. 8A-8C, flowcharts 80, 82, and 84 of steps for reconstruction of 4D tomosynthesis datasets are depicted. Each of the captured projection images 802 may be pre-processed 803 and buffered in on-board GPU memory or a combination of system and GPU memory (e.g., memory buffered projections 804). The memory buffered projections 804 are then indexed 805 for retrieval. According to the desired projection subset size 806 and time point 808, the software pulls the appropriate projections/projection subsets 810 at particular timepoints from the indexed projections 805 into the reconstruction calculation. The reconstruction computation 812 then takes place, followed by post-processing 814 to generate the reconstructed image 816. Since the reconstruction process is dynamic, both the projection subset size 806 and timepoint 808 can be interactively changed by the user along with all the other reconstruction and filtering parameters. The subset size 806 can be varied from 1 to number of projections in a single acquisition cycle.

To improve computation efficiency as depicted in flowcharts 82 and 84, the reconstruction can take advantage of the fact that some projections remain constant between nearby timepoints. Backprojection computations from individual projections may be buffered. This allows different timepoints to be reconstructed by reusing the buffered backprojections from the projections which remain constant and only performing the backprojection for the updated projections at the new timepoint. As shown in flowchart 82, the first reconstruction timepoint processes the projection subset at timepoint t 821 and sends the projection subset to be reconstructed 823. Each of the projections in the subset 821 is computed as a backprojection 824 and in stored in the backprojection buffer memory 826. Then, as depicted in flowchart 84, the backprojection 824 stored in the backprojection buffer 826 is reused for reconstruction at the next time point. Backprojections 2 through M can be pulled from the backprojection buffer 826, and only the new backprojection M+1 needs to be computed in 824 for the updated timepoint. Such features may be conducted in real-time. In such embodiments, reconstruction in 3D is started once sufficient data is accumulated to make the first reconstruction. After the image is acquired, the image is moved to a buffer and the 3D image is updated immediately. Thus, the 3D data is periodically (e.g., once per image acquisition) and automatically updated. These real-time modes may be utilized in real-time biopsy needle guidance implementations.

The software processes described above may also be implemented with other tomographic reconstruction methods such as filtered backprojection, backprojection filtering, and iterative methods.

The reconstruction flexibility opens up several options. If a higher spatial resolution image is desired, the user may elect to trade-off some temporal resolution and reconstruct using a larger subset size (e.g., larger window). Conversely, if a higher temporal resolution is desired, the user can trade off some spatial resolution by using a smaller projection subset size (e.g., smaller window). In an embodiment, the CETI reconstruction software permits the user to select which projections are used at each time point to create each individual 3D image. The number of projections used for each reconstruction may be increased or decreased. Increasing the number of projections for a reconstruction increases tomographic resolution while decreasing temporal resolution. As such, a user may select a larger number of projections to increase the tomographic resolution with the trade-off that the temporal resolution would decrease when such an increase in tomographic resolution is desired. Accordingly, the user may decrease the number of projections to improve the temporal resolution when improved temporal resolution is desired over improved tomographic resolution. Advantageously, by varying the selection of the number of projections that are used to create each image at each time point, the user may dynamically alter the degree of tomographic and temporal resolution as desired to achieve each 4D reconstruction. Filtering can also be dynamically adjusted to changes in the reconstruction. For example, the noise filtering can be dynamically adjusted to compensate for magnification or projection subset size changes.

Additionally, each projection is shown such that the plane of interest is portrayed at the plane of a display (e.g., a video monitor) configured to output the image and adapted to operate with the CETI reconstruction software. This advantageously provides a system in which the object of interest and the plane of the object of interest is held fixed on the display while other objects in different planes are permitted to move, providing a rendering with a 3D appearance on a 2D projection of images.

Figure 9:
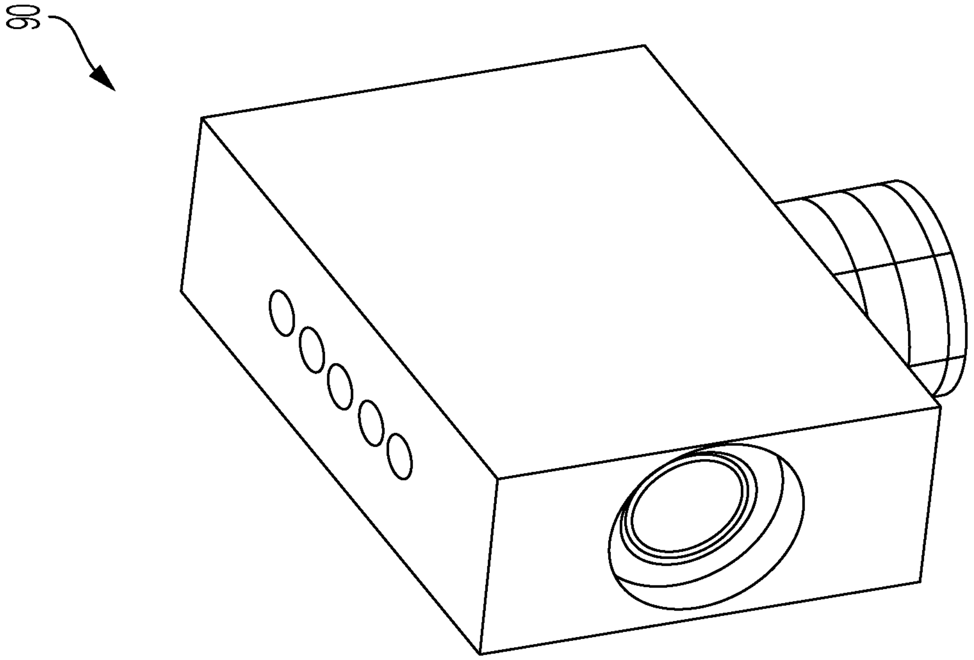
FIG. 9 is a perspective view of a phantom for use in testing the 4D image acquisition system in accordance with aspects of the invention.

FIG. 9 depicts a phantom 90. The phantom 90 mimics the flow of contrast agent through human tissue and is used to generate the data depicted in FIGS. 3A-7D in place of object 26 (e.g., human tissue, a patient, etc.). In an embodiment, the phantom 90 is constructed of Lucite (and/or other tissue mimicking the structure and appearance of plastic) and may be of a size and thickness of the object being imaged (e.g., about 200 square centimeters and about 5 centimeters in thickness for breast imaging). The phantom 90 may include a single cylindrical chamber that spans the width of the phantom 90 to simulate a vessel. In one embodiment, the phantom includes attachments at each end to connect to a pump and a reservoir to simulate the action of a heart of a patient (e.g., to pump fluid through the cylindrical chamber). A contrast agent (or other background fluid) may be injected into the tubing of the phantom 90 to simulate the inflow and outflow of the contrast agent such that the phantom 90 is able to provide dynamic flow. The illustrated phantom 90 enables pumping of fluid (e.g., contrast agent) with a time-varying concentration through a central chamber. Along the top edge of the phantom 90 are closed cylindrical chamber of various diameters utilized for calibration standards.

Experiments were conducted in which a time-varying concentration of contrast agent was continuously pumped through the phantom 90 and a series of projection images were acquired over a 32 degree angular range with one projection every 2 degrees. Reconstructions were performed using a sliding window of 17 projections.

Figure 10:
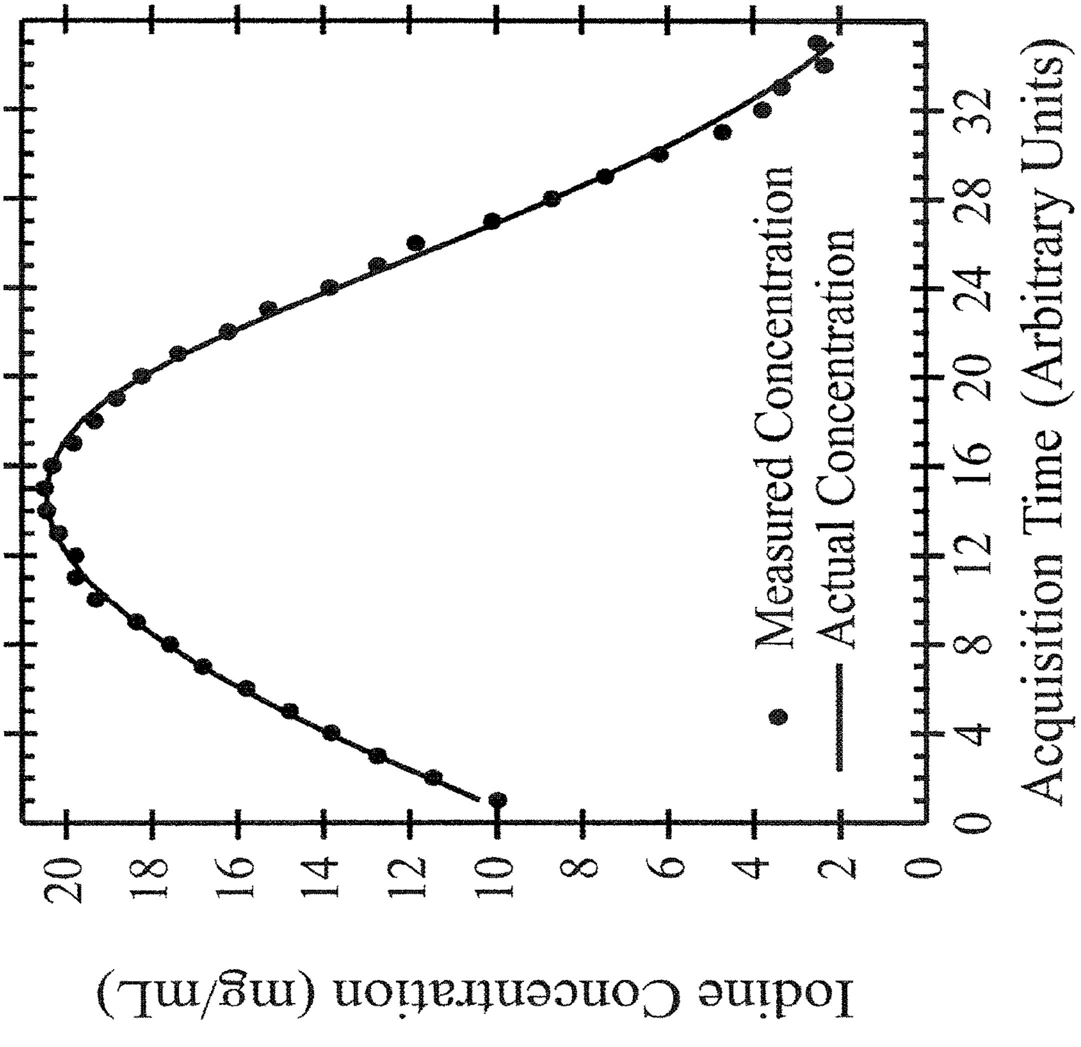
FIG. 10 is a graph comparing observed concentration over time to actual concentration over time within the phantom in accordance with aspects of the invention.

Reconstruction data was analyzed to determine the observed contrast concentration in the phantom 90. FIG. 10 is a graph 1000 illustrating a comparison between observed concentration over time to the actual concentration over time. The results illustrate close agreement between the expected and observed data.

Figure 11:
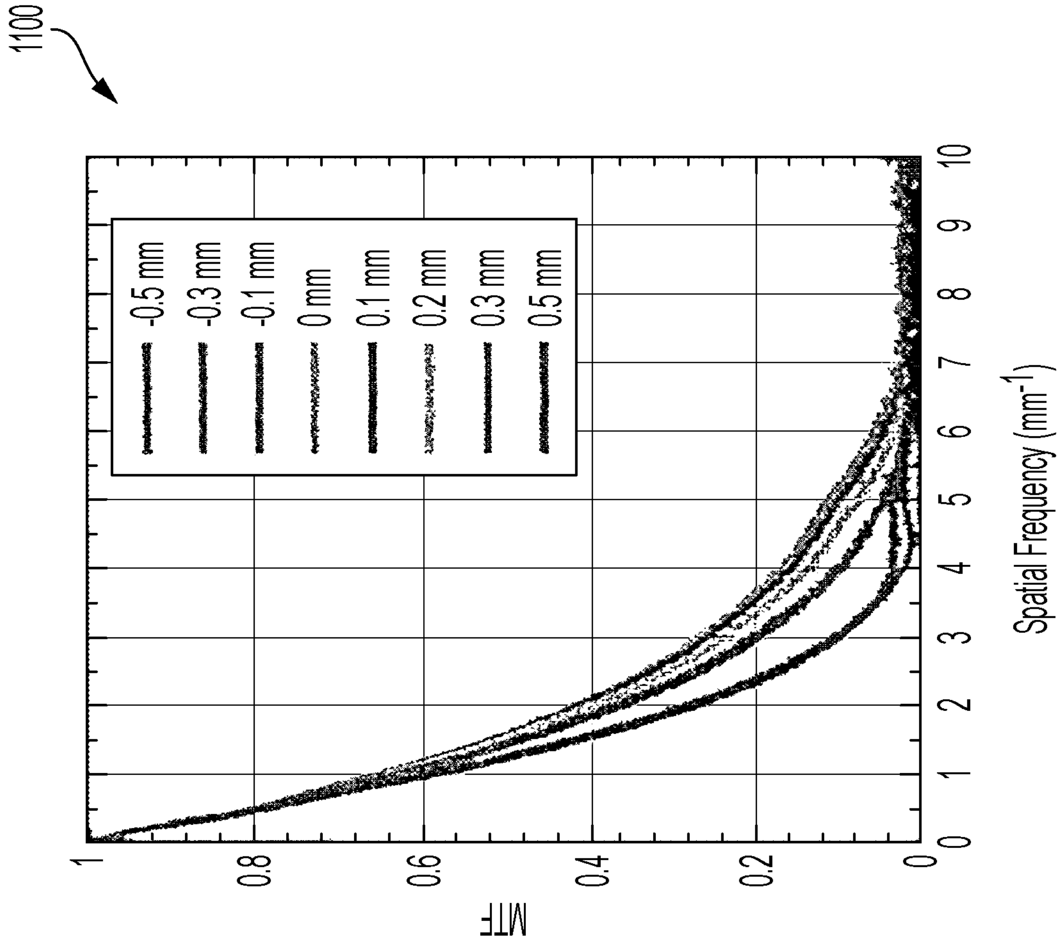
FIG. 11 is a graph characterizing spatial resolution of the 4D image acquisition system in accordance with aspects of the invention.

The spatial resolution of the system was characterized by analyzing the modulation transfer function (MTF). Sample data of the MTF at different distances between the reconstruction plane and an object of interest are shown in the graph 1100 depicted at FIG. 11.

Figure 12:
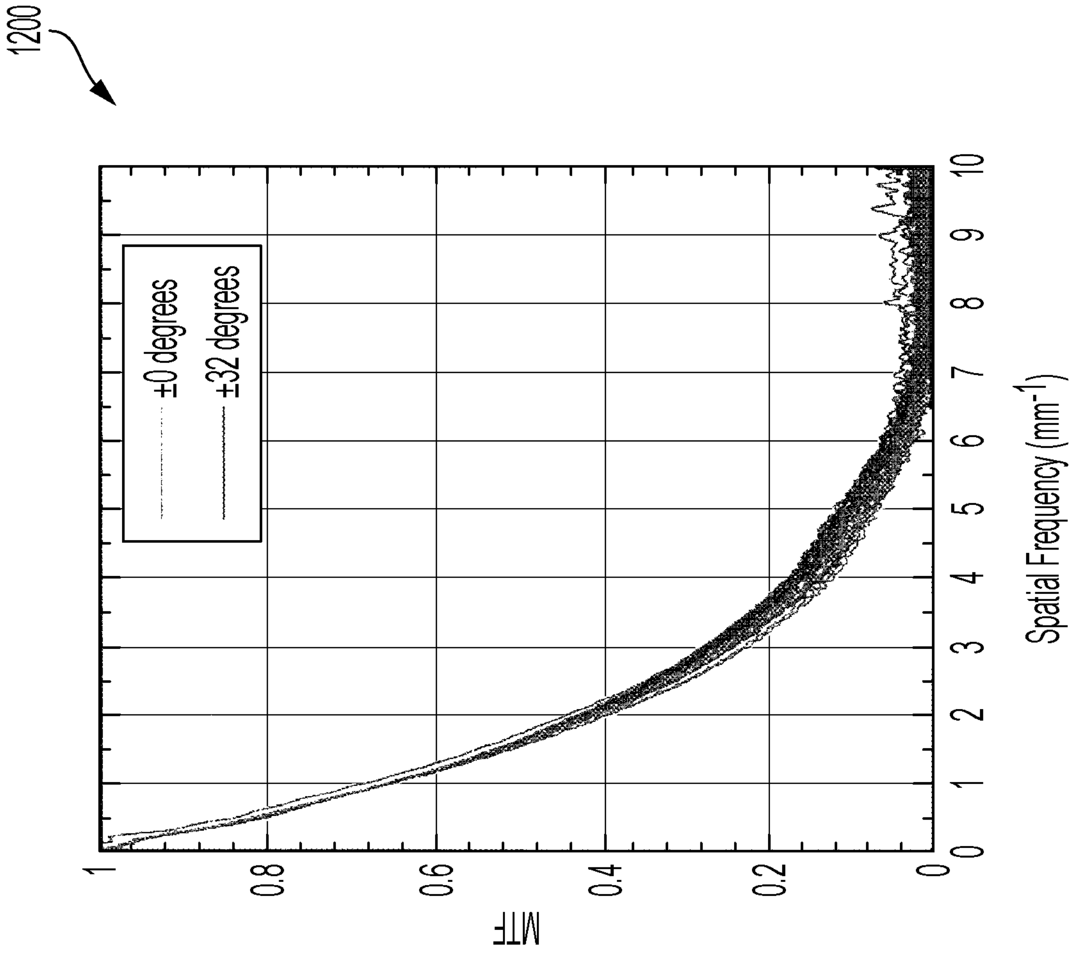
FIG. 12 is a graph characterizing MTF over spatial frequency for various angles in accordance with aspects of the invention.

At FIG. 12, a graph 1200 depicting MTF versus frequency is shown. FIG. 12 shows the distribution of MTFs across a 640 range of reconstruction slice angles (−320 to 320 with respect to the plane parallel with the detector, in 20 increments). There exists a distinct trend in the data showing that the MTF degrades 360 as the obliquity of the reconstruction plane increases, shown in FIG. 12 by the transition from superior to inferior curves. The variation in the MTF with angular range is very small (compare with FIG. 11). This supports the assertion that the time point and window size can be varied in the reconstruction.

Figure 13:
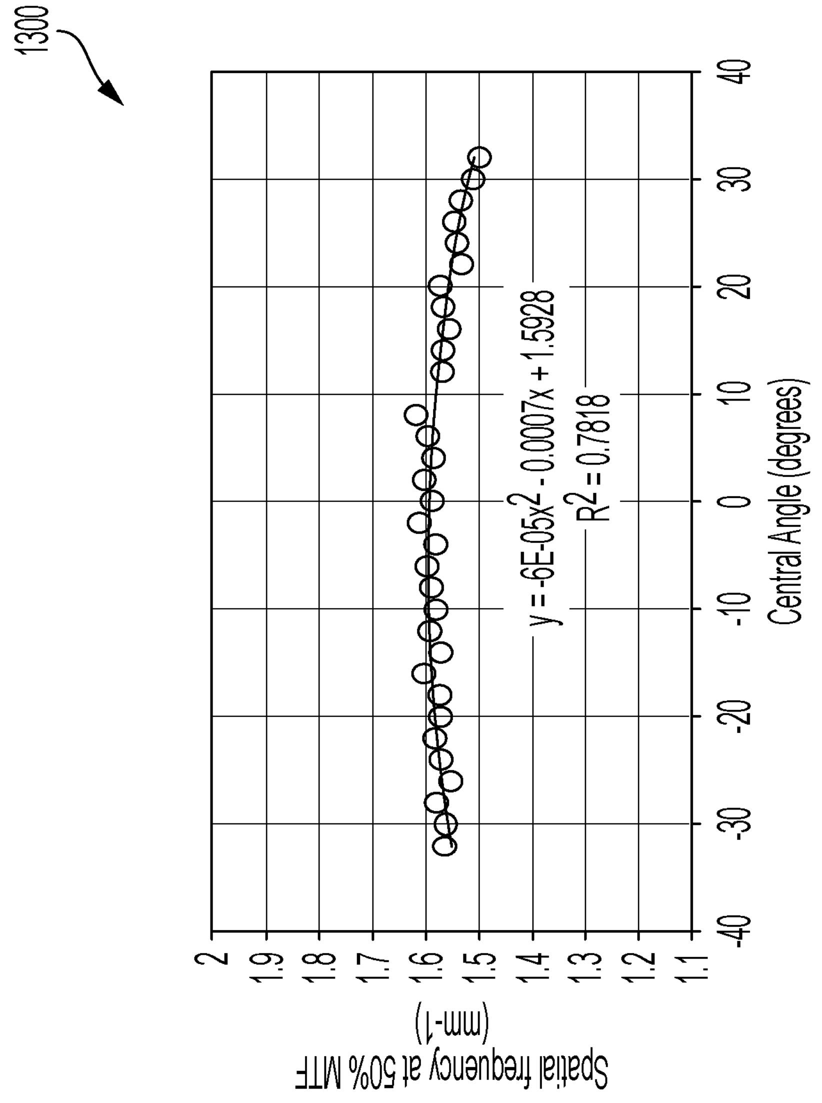
FIG. 13 is a graph characterizing spatial frequency at 50% MTF versus central angle according to aspects of the invention.

At FIG. 13, a chart 1300 depicting central angle versus spatial frequency is shown. The frequency at which the MTF drops below 50% of its maximum value is plotted for each of the 33 different reconstruction slice angles in FIG. 13. The trend is clearly visible in this figure. A second order polynomial fit was plotted through this data as shown in FIG. 13. In an ideal system, the peak of the hyperbola would be located at 0°, but some outliers and noise exist in the data. FIG. 12 shows that the MTF drops by 4.1% when comparing the peak MTF to the MTF at a 320 obliquity from the peak, based on the trendline data.

Figure 14:
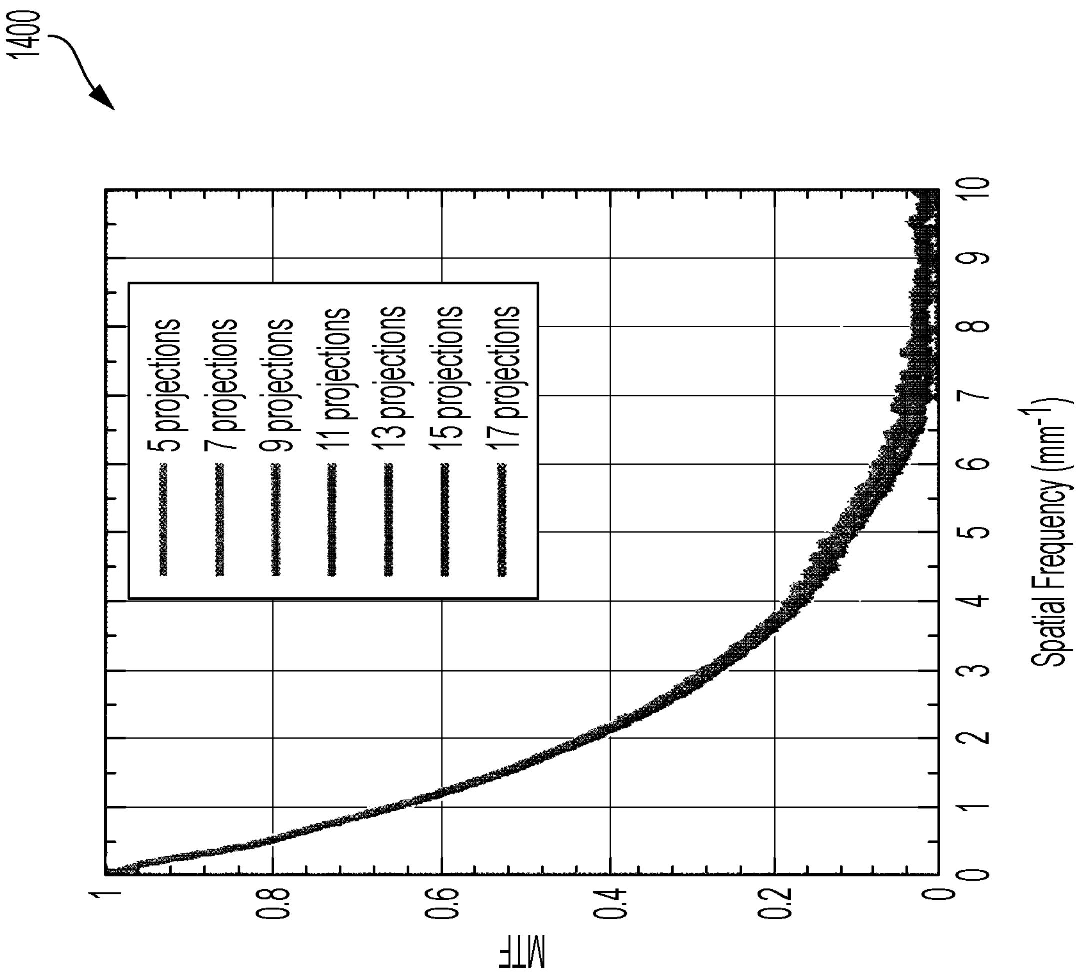
FIG. 14 is a graph characterizing MTF versus spatial frequency for various numbers of projections in accordance with aspects of the invention.

FIG. 14 is a graph 1400 showing the variation of spatial frequency versus MTF. FIG. 14 shows the MTF in the plane of the test tool for a varying number of projections used to create the reconstruction. There is little change in the MTF as the number of projections changes, and there is no distinguishable trend so long as the angular range remains the same. This appears to be true regardless of which n projections are used to reconstruct a subset of size n; that is, given a set of 17 projections, a reconstruction using any 5 of them will produce the same MTF as if all 17 projections were used in the reconstruction, provided the outer-most projection angles are included in the five. The variation in the MTF with number of projections is very small (compare with FIG. 11). This supports the assertion that the time point and window size can be varied in the reconstruction.

The experiments and analysis demonstrate that it is feasible to perform reconstructions from oblique projection sets without significant degradation of the in-plane resolution. Further, these data explicitly demonstrate that the reconstructed images support super-resolution in combination with functional (flow) information.

In addition, the imaging systems, methods, and devices disclosed above may be utilized in additional applications. For example, a surgical instrument (e.g., a biopsy needle) may be inserted into a patient, a series of images of the tissue of the patient are acquired at various angles, and 4D images are constructed for the surgical instrument relative to the tissue of the patient. When such images are combined with real-time reconstruction, the image data may provide a physician (or a robotic positioning system) with real-time guidance information to direct the surgical procedure (e.g., a tissue biopsy), and to monitor the removal of the tissue of interest.

Another example includes injecting, optionally, a contrast agent into an object of interest, acquiring a series of images of the object over various angles, with one image is acquired for each angle. 4D image data for the object may be constructed from the acquired series of images. Such applications may be utilized in monitoring of flow in pipes, tubes, pipelines, etc., where the material under examination may have sufficient intrinsic radiographic contrast so that an exogenous contrast material is not required. Additionally, the object may include material that, under examination, lacks sufficient intrinsic radiographic contrast, so that an exogenous contrast material is required.

Another example includes bolus tracking. Bolus tracking is a method in which low dose images are made with reduced frequency. These images are analyzed for the presence of the contrast agent. Once contrast agent is sensed in the image, images with higher dose and higher frequency are acquired for clinical use. In this way, the patient radiation dose is minimized and the timing of the image relative to the appearance of the contrast agent is improved.

Furthermore, the systems, methods, and devices may also be utilized to observe objects under motion in 3D as a function of time. As an example, the motion of airplane control surfaces may be observed to search for faults in the structure of the wing as a function of the control surface position.

Although the invention has been described above with reference to imaging tissue, especially breast tissue, in a human body, the invention has broader applicability. For example, the inventive concepts described herein may be used for nondestructive testing, e.g., it could be used for pipelines, etc. to assess flow in real time—oil pipelines, etc, may use technology to check for inclusions in the pipes that could cause problems. Suitable modification will be understood by one of skill in the art from the description herein.

Although the invention is illustrated and described herein with reference to specific embodiments, the invention is not intended to be limited to the details shown. Rather, various modifications may be made in the details within the scope and range of equivalents of the claims and without departing from the invention.

The invention claimed is:

1. A digital tomosynthesis method for guided use of a surgical instrument, the method comprising:

acquiring, while a surgical instrument is inserted into an object and at a plurality of time-points, a series of projection images of the object, each of the projection images being associated with a corresponding time-point of a plurality of time-points, and the series of projection images being acquired over the plurality of time-points and at a plurality of angles, wherein at each time-point, a plurality of projection images are acquired, and wherein the plurality of projection images corresponds to a subset of angles less than the plurality of angles; and constructing four dimensional image data from the series of projection images, wherein the four dimensional image data comprises a representation of the object from each of the plurality of angles for each of the plurality of time-points, wherein constructing the four dimensional image data comprises combining projection images from a first acquisition cycle with projection images from a second acquisition cycle.

2. The method of claim 1, further comprising causing the surgical instrument to be inserted into the object.

3. The method of claim 1, wherein the surgical instrument comprises a biopsy needle.

4. The method of claim 1, further comprising: providing the four dimensional image data as guidance information for a surgical procedure associated with the surgical instrument.

5. The method of claim 4, wherein providing the four dimensional image data as guidance information for the surgical procedure comprises at least one of: directing a robotic positioning system for the surgical procedure, and causing display, via user interface, of the four dimensional image data.

6. The method of claim 1, wherein the series of projection images are acquired using contrast enhancement based on a contrast agent in the object.

7. The method of claim 1, further comprising positioning, for the acquiring of the series of projection images, one or more of: a detector comprising an array of pixels, at least a portion of the object, or at least one source of penetrating particles.

8. The method of claim 1, wherein constructing the four dimensional image data from the series of projection images comprises for each time-point of the plurality of time-points, generating a reconstruction based on a subset of the series of projection images.

9. The method of claim 8, further comprising:

adjusting, for a time-point of the plurality of time-points and associated subset, a subset size to adjust temporal and spatial resolution at the time-point of the plurality of time-points of the four dimensional image data; and providing updated four dimensional image data based on the adjusted subset size.

10. The method of claim 1, wherein constructing the four dimensional image data from the series of projection images comprises for each time-point of the plurality of time-points, generating a multi-planar reconstruction based on a subset of the series of projection images.

11. The method of claim 1, wherein constructing the four dimensional image data from the series of projection images comprises for each time-point of the plurality of time-points, generating a reconstruction along a surface based on a subset of the series of projection images.

12. The method of claim 1, wherein the four dimensional image data exhibits super-resolution.

13. A digital tomosynthesis device for guided use of a surgical instrument, the device comprising:

one or more processors; and memory storing instructions that, when executed by the one or more processors, cause the device to:

acquire, while the surgical instrument is inserted into an object and at a plurality of time-points, a series of projection images of the object, each of the projection images being associated with a corresponding time-point of a plurality of time-points, and the series of projection images being acquired over the plurality of time-points and at a plurality of angles, wherein at each time-point, a plurality of projection images are acquired, and wherein the plurality of projection images corresponds to a subset of angles less than the plurality of angles; and construct four dimensional image data from the series of projection images, wherein the four dimensional image data comprises a representation of the object from each of the plurality of angles for each of the plurality of time-points, wherein constructing the four dimensional image data comprises combining projection images from a first acquisition cycle with projection images from a second acquisition cycle.

14. The device of claim 13, wherein the instructions, when executed by the one or more processors, further cause the device to cause the surgical instrument to be inserted into the object.

15. The device of claim 13, wherein the surgical instrument comprises a biopsy needle.

16. The device of claim 13, wherein the instructions that, when executed by the one or more processors, further cause the device to provide the four dimensional image data as guidance information for a surgical procedure associated with the surgical instrument.

17. The device of claim 16, wherein the instructions that, when executed by the one or more processors, cause the device to provide the four dimensional image data as guidance information for the surgical procedure comprises instructions that, when executed by the one or more processors, cause at least one of: the device to direct a robotic positioning system for the surgical procedure, and the device to cause display, via a user interface, of the four dimensional image data.

18. The device of claim 13, wherein the series of projection images are acquired using contrast enhancement based on a contrast agent in the object.

19. The device of claim 13, wherein the instructions, when executed by the one or more processors, further cause the device to position, for the acquiring of the series of projection images, one or more of: a detector comprising an array of pixels, at least a portion of the object, or at least one source of penetrating particles.

20. The device of claim 13, wherein the instructions that, when executed by the one or more processors, cause the device to construct the four dimensional image data from the series of projection images comprises instructions that, when executed by the one or more processors, cause the device to for each time-point of the plurality of time-points, generate a reconstruction based on a subset of the series of projection images.

21. The device of claim 20, wherein the instructions, when executed by the one or more processors, further cause the device to:

adjust, for a time-point of the plurality of time-points and associated subset, a subset size to adjust temporal and spatial resolution at the time-point of the plurality of time-points of the four dimensional image data; and provide updated four dimensional image data based on the adjusted subset size.

22. The device of claim 13, wherein the instructions that, when executed by the one or more processors, cause the device to construct the four dimensional image data from the series of projection images comprises instructions that, when executed by the one or more processors, cause the device to for each time-point of the plurality of time-points, generate a multi-planar reconstruction based on a subset of the series of projection images.

23. The device of claim 13, wherein the instructions that, when executed by the one or more processors, cause the device to construct the four dimensional image data from the series of projection images comprises instructions that, when executed by the one or more processors, cause the device to for each time-point of the plurality of time-points, generate a reconstruction along a surface based on a subset of the series of projection images.

24. A digital tomosynthesis system for guided use of a surgical instrument, the system comprising:

a surgical instrument; and a computing device configured to:

acquire, while the surgical instrument is inserted into an object and at a plurality of time-points, a series of projection images of the object, each of the projection images being associated with a corresponding time-point of a plurality of time-points, and the series of projection images being acquired over the plurality of time-points and at a plurality of angles, wherein at each time-point, a plurality of projection images are acquired, and wherein the plurality of projection images corresponds to a subset of angles less than the plurality of angles; and construct four dimensional image data from the series of projection images, wherein the four dimensional image data comprises a representation of the object from each of the plurality of angles for each of the plurality of time-points, wherein constructing the four dimensional image data comprises combining projection images from a first acquisition cycle with projection images from a second acquisition cycle.

* * * * *